United States Patent [19]
Romaschin et al.

[11] Patent Number: 5,804,370
[45] Date of Patent: Sep. 8, 1998

[54] EARLY DIAGNOSIS OF SEPSIS UTILIZING ANTIGEN-ANTIBODY INTERACTIONS AMPLIFIED BY WHOLE BLOOD CHEMILUMINESCENCE

[75] Inventors: Alex D. Romaschin, Etobicoke; Paul M. Walker, Toronto, both of Canada

[73] Assignee: Critichem Medical Products Limited, Toronto, Canada

[21] Appl. No.: 552,145

[22] Filed: Nov. 2, 1995

Related U.S. Application Data

[63] Continuation-in-part of Ser. No. 516,204, Aug. 17, 1995, abandoned, which is a continuation of Ser. No. 257,627, Jun. 8, 1994, abandoned.

[30] Foreign Application Priority Data

Jun. 8, 1994 [WO] WIPO ............ PCT/CA94/00325

[51] Int. Cl.$^6$ .................................. C12Q 1/70
[52] U.S. Cl. .................. 435/5; 435/7.1; 435/7.2; 435/7.24; 435/7.31; 435/7.32; 435/24; 435/34; 435/962; 435/968; 435/975; 436/513; 436/518; 436/536; 436/808; 436/811
[58] Field of Search ................. 435/5, 7.1, 7.2, 435/7.24, 7.31–7.37, 25, 34, 38, 962, 968, 973, 975; 436/513, 518, 536, 539, 808, 811

[56] References Cited

U.S. PATENT DOCUMENTS

| | | | |
|---|---|---|---|
| 4,647,532 | 3/1987 | Watanabe et al. | 435/28 |
| 4,737,455 | 4/1988 | De Baetselier | 435/7.1 |
| 4,959,302 | 9/1990 | Cornaby et al. | 435/5 |
| 5,108,899 | 4/1992 | Allen | 435/7.21 |
| 5,210,019 | 5/1993 | Margalit | 435/7.32 |
| 5,294,541 | 3/1994 | Kaplan et al. | 435/29 |

FOREIGN PATENT DOCUMENTS

| | | |
|---|---|---|
| 0430440 | 10/1990 | European Pat. Off. . |
| 2131948 | 5/1983 | United Kingdom . |
| WO 90/06514 | 6/1990 | WIPO . |
| WO 92/03734 | 3/1992 | WIPO . |
| WO 92/16553 | 10/1992 | WIPO . |
| WO 94/29728 | 12/1994 | WIPO ................... 435/5 |

OTHER PUBLICATIONS

Lilius et al., "Leukocytes as Immunosensors: An Immunoassay Without Labelled Reagents", J. Biolumin. Chemilumi, 7(2): 117–122, Apr. 1992.
Romaschin, et al., "A Rapid Whole Blood Assay for Gram Negative Endotoxin Utilizing Chemiluminescence Detection", Clin Chem, 42 (6 part 2) A146, 1996.
Michie (1992) Proc. Brussels Symp., pp. 329–338.
Winkelhake et al. (1992) J. Infect. Dis. 165:26–33.
Zeller et al. (1992) J. Leukocyte Biol. 52:449–55.
Ziegler et al. (1991) New England J. Medicine 324(7):429–36.

*Primary Examiner*—Carol A. Spiegel
*Attorney, Agent, or Firm*—Klauber & Jackson

[57] ABSTRACT

The invention relates to a method for determining the extent of sepsis and/or an infection in a human or animal patient by detecting the amount of an antigen indicative of such infection. The amount of the antigen is detected in a patient blood derived test sample containing blood cell fractions. The method comprises:

i) incubating the test sample with an amount of test antibodies specific to the antigen indicative of sepsis and/or infection to form antibody/antigen complexes;

ii) allowing the antibody/antigen complexes to interact with the white blood cell fractions which results in the production of oxidants;

iii) introducing to either steps i) or ii) a chemiluminescent compound to the test sample;

iv) allowing the oxidants to react with the chemiluminescent compounds to emit luminescent light from the test sample;

v) measuring the amount of emitted light over a predetermined period; and vi) correlating extent of sepsis and/or infection by comparison of the measured amount of emitted light of the test sample with measured amount of light emitted by a control sample which is treated the same as the test sample for steps i) to v) except that in step i) control antibodies are used which are of the same class as the test antibodies but are non-specific to the antigens indicative of infection.

38 Claims, 11 Drawing Sheets

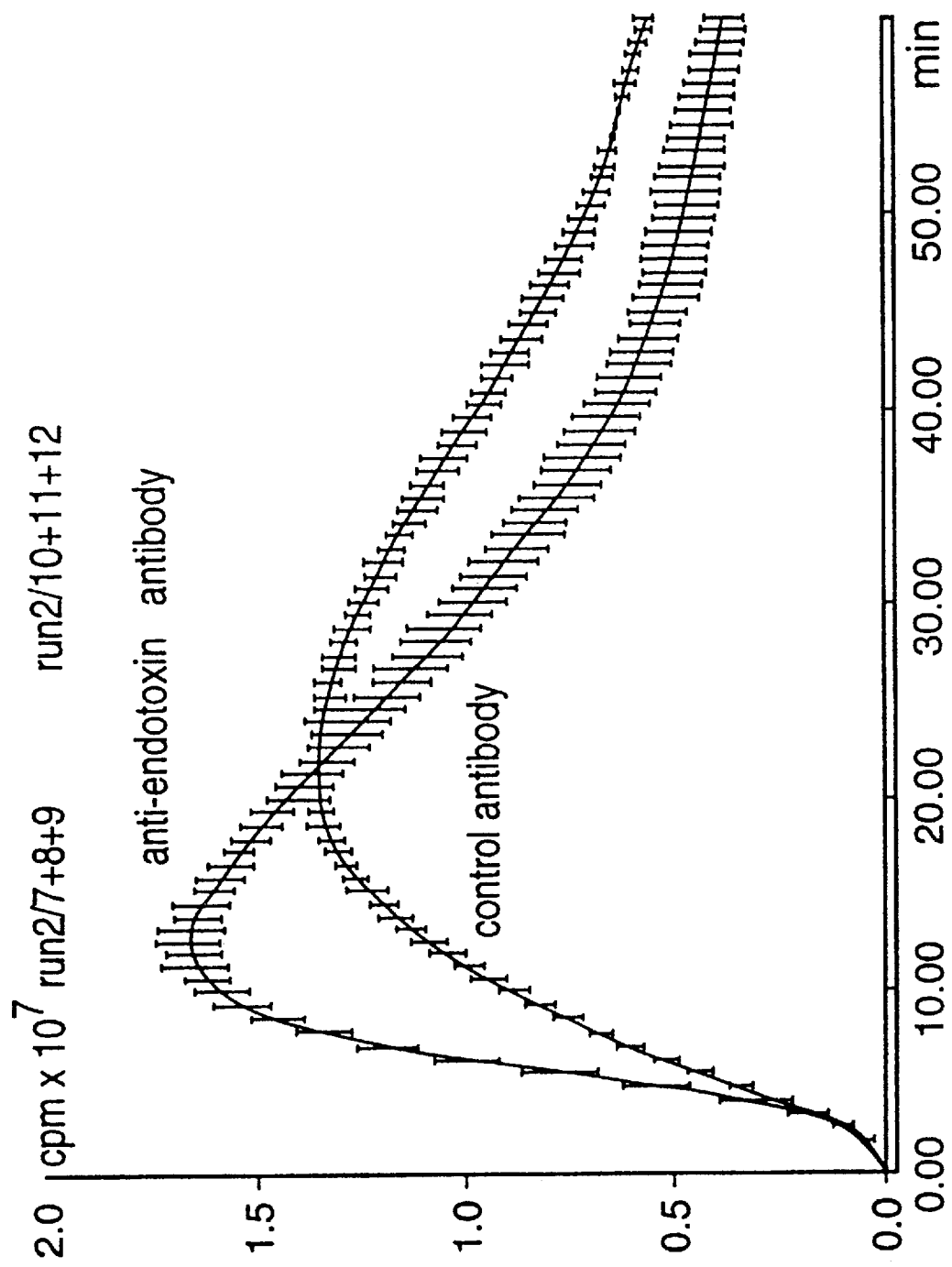

EARLY DIAGNOSIS OF SEPSIS UTILIZING ANTIGEN-ANTIBODY INTERACTIONS AMPLIFIED BY WHOLE BLOOD CHEMILUMINESCENCE

CROSS-REFERENCE TO RELATED APPLICATIONS

This application is a continuation-in-part of application Ser. No. 08/516,204, filed Aug. 17, 1995, now abandoned, which is a continuation of application Ser. No. 08/257,627, filed Jun. 8, 1994 now abandoned, which is a national stage entry of PCT/CA94/00325 filed Jun. 8, 1994, and which claims priority of Canadian Application Serial No.2,097,952, filed Jun. 8, 1993.

FIELD OF THE INVENTION

This invention relates to a rapid diagnostic screening technology to allow biochemical staging of a patient's infection or septic progression so that an appropriate therapeutic intervention strategy can be identified and initiated.

BACKGROUND OF THE INVENTION

Hospital and particularly intensive care unit patients who have acquired nosocomial infections as a result of peri- or post-operative immunosuppression or secondary to other disease processes, such as, pancreatitis, hypotensive or hypovolemic shock, physical trauma, burn injury, or organ transplantation, and develop septic shock syndrome have a mortality which has been quoted to range from 30–70% depending upon other co-incident complications. Until the recent advent of novel new therapeutic strategies these patients have been managed largely by palliative care and administration of antibiotics. The growth of biotechnology has allowed the large scale production of many new target directed biopharmaceuticals which utilize monoclonal antibodies against such initiators of sepsis as gram-negative endotoxin (Centocor's HA-1A or Xoma's Xomen-E5), tumor necrosis factor (various producers including Hoffman LaRoche, Centocor with patents WO 90/06514 and WO 92/16553), interleukins and various soluble receptor antagonists such as IL-1 RA (Synergen) and $SCR_1$ (soluble complement receptor 1)—a truncated recombinant complement regulatory molecule.

Despite the development of increasingly potent antimicrobial agents, the incidence of nosocomial infections and, in particular, infections leading to sepsis or septicemia is increasing. The difficulty with many of the promising therapeutic agents is that their window of opportunity and indications for use have not been adequately delineated largely due to a lack of appropriate rapid diagnostic procedures and partly due to a lack of complete understanding of the pathogenesis of the sepsis syndrome. The cost of these therapeutic agents is significant, being priced at $3,000.00 to $4,000.00 per dose. Thus providing this therapy indiscriminately to patients would add a considerable burden to the health care system without providing a corresponding benefit to patients.

Currently, one of the major problems with many of the therapeutic protocols being tested by the pharmaceutical companies conducting clinical trials in sepsis intervention is their inability to rapidly detect early and evolving sepsis. The results of blood cultures may arrive too late. Other septicaemia tests are also time consuming and may not be sensitive enough for early detection. Centocor Inc.'s immunometric assay for tumor necrosis factor-alpha (TNF-α) uses two antibodies, one of which is labelled (WO 90/06314). The National Aeronautics and Space Administration detects Pseudomonas bacteria by extraction of Azurin and detection using Azurin-specific antibody (U.S. Pat. No. 7,501,908). The endotoxin assay kit purchased from BioWhittaker (Walkerville, Md., U.S.A.) or Seikagaku Kogyo Ltd. (Tokyo, Japan) is a Limulus Amebocyte Lysate Assay technique which may be used as a comparison for the present invention.

Many investigators versed in the complexities of the septic response believe that treatment is ineffectual for patients who already manifest the classical clinical symptoms of sepsis (i.e., hyperdynamic circulation, hypotension, decreased systemic vascular resistance, pyrexia and increased oxygen dependency). The course of the inflammatory process has progressed too far for many of the interventions to benefit the patient since the multiple interacting inflammatory cascades which attempt to eliminate the infectious challenge are in many instances at their nadir and difficult to control pharmacologically. A major clinical and diagnostic challenge is to identify and stage patients, ideally early in the progression of the septic response, or to identify those patients at high risk of developing fulminant sepsis syndrome. The same therapeutic agents given at the appropriate stage in the septic process may have more significant beneficial effects since it is clear that an optimal window period may exist for the efficacy of any particular therapeutic agent. For example, giving a patient antibodies or receptors directed against gram-negative endotoxins when the patient has no detectable levels of these agents present in the circulation and already has a maximally activated cytokine cascade is a waste of resources and of no benefit to the therapy of the patient. The potential market for these antisepsis strategies remains large (about 250,000 cases per year in the USA) and has been limited by the inability to identity and stage patients who could benefit from the appropriate pharmacologic interventions.

In accordance with this invention, a new rapid diagnostic screening technology is provided which determines biochemical staging of a patient's septic progression so that the appropriate therapeutic intervention strategy can be rapidly identified and initiated utilizing either single or multiple agents. Such an approach optimizes the potential cost benefit ratio by systematically and biochemically identifying patients who would potentially benefit from target affected antisepsis therapy. The lack of such rapid testing strategies combined with the high unit dose cost of many of the new therapies ($3,700.00 US per dose for Centocor HA-1A human IgM antibody) has had a seriously limiting effect on FDA approval. The present invention's analytical approach provides the early diagnostic information necessary for rapid and rational decision making.

Sepsis is defined as the presence of pathogenic microorganisms or their toxins in the blood or other tissues. Septic shock is shock that may develop as a result of a severe infection. Between 60% to 70% of septic shock cases are caused by Gram-negative aerobic bacilli infections. Since both the incidence and mortality accompanying shock are higher in Gram-negative than Gram-positive infections, most therapy research has been directed to combatting septic shock due to Gram-negative septicemia.

A significant area of therapeutic research is in the development of antibiotic therapy. Although antibiotics do not prevent the toxic effects of endotoxin (and may stimulate the release of endotoxin from bacteria during cell killing), it has been clearly demonstrated that the judicious administration of antibiotics can significantly increase survival, with up to a 50% reduction in the occurrence of shock.

Immunomodulating substances are released as part of the non-specific host immunoinflammatory defense mechanism to Gram-negative infections. Some of these substances are mediators of the toxic effects of endotoxin and researchers have developed monoclonal antibodies, receptor antagonists and other agents directed to them. Once again, successful therapy with these immunologic agents depends on their timely administration.

Another sepsis therapeutic treatment involves treatment with monoclonal antibodies directed against lipid A. Two such products are HA-1A (Centoxin) developed by Centocor (Zeigler, E. J., et al., *N. Engl. J. Med.* 429:324 (1991); Michie, H. R. Proceedings of Brussels Sym. 329 (1992)) and murine IgM MAbES (Xomen-E5) developed by Xoma. Given the high price of these treatments, it is essential to predict whether this therapy will even benefit the patient. Further, because Centoxin and Xoma-E5 are only effective in gram-negative septicemia, they will be potentially ineffective in almost 50% of the cases in which they are administered if clinical symptoms are the major criterion for use.

Often the clinical signs of sepsis and sepsis syndrome (the earliest stages) are recognized long before results of blood or other body fluid cultures are available. Without a comprehensive diagnostic test, which is desirably carried out at bedside to indicate sepsis and its level of progression, many patients may be treated unnecessarily or with an inappropriate therapeutic regime. In many patients, initiation of monoclonal antibody therapy against gram-negative endotoxin on the basis of clinical symptoms such as profound hypotension, hyperdynamic circulation, pyrexia, etc., may be too late in the disease process. Since many of the proximal cytokine mediators of sepsis are likely to be maximally recruited, effective blockade of the cytokine response or blunting of the initiating effects of endotoxin must be entertained during the early pre-clinical phase. Identification of this early initiating phase of sepsis may be achieved with the present invention's rapid and sensitive assay for both gram-negative and gram-positive endotoxins. If the test is not rapid, the time span of several hours may be sufficient to drive the progression of early profound endotoxin challenge to irreversible sepsis. For this reason the present diagnostic strategy is beneficial in providing rapid and if necessary, repetitive feedback regarding septic progression. The present invention provides the comprehensive diagnostic test needed to determine the proper therapy for the patient with sepsis by quantitatively measuring antigen and mediator levels in the blood. The present invention is equally effective for measuring any antigen present in the blood. Thus the present invention can be employed to measure the level of antigens in blood, to provide staging of an infection.

The analytical approach of this invention allows the rapid diagnosis and staging of patients who have this devastating syndrome by harnessing the patients' own recognitive systems to help amplify the analytical signal. This diagnostic approach also constitutes a rapid test for evaluating the efficacy of antibodies directed against specific antigens in whole blood.

This invention takes advantage of the specificity of antigen-antibody interactions and the high sensitivity of chemiluminescent light emission which is triggered in white blood cells through the generation of oxidants and their excitation of a chemilumiphor. A sensitive and generic approach to the detection of sepsis related antigens is thereby provided.

Allen, U.S. Pat. No. 5,108,899 also describes the use of chemiluminescence to detect oxidant production. However, Allen accomplishes this aspect in a different way for a somewhat different purpose as will be described in respect of the detailed discussion of the inventive preferred embodiments.

SUMMARY OF THE INVENTION

According to an aspect of the invention, a method for determining the extent of an infection in a human or animal patient by detecting the amount of an antigen indicative of such infection. The amount of the antigen is detected in a patient blood derived test sample containing blood cell fractions. The method comprises:

i) incubating the test sample with an amount of test antibodies specific to the antigen indicative of infection to form antibody/antigen complexes;

ii) allowing the antibody/antigen complexes to interact with the white blood cell fractions which results in the production of oxidants;

iii) introducing to either steps i) or ii) a chemiluminescent compound to the test sample;

iv) allowing the oxidants to react with the chemiluminescent compounds to emit luminescent light from the test sample;

v) measuring the amount of emitted light over a predetermined period; and vi) correlating extent of infection by comparison of the measured amount of emitted light of the test sample with measured amount of light emitted by a control sample which is treated the same as the test sample for steps i) to v) except that in step i) control antibodies are used which are of the same class as the test antibodies but are non-specific to the antigens indicative of infection.

According to another aspect of the invention, a method is provided for determining the extent of sepsis in a human or animal patient by detecting the amount of sepsis associated markers in a patient blood derived test sample containing white blood cell fractions. The method comprises:

i) incubating the test sample with an amount of test antibodies specific to a selected sepsis-associated marker to form antibody/marker complexes;

ii) allowing the antibody/marker complexes to interact with the white blood cell fractions which results in the production of oxidants;

iii) introducing to either steps i) or ii) a chemiluminescence compound to the test sample;

iv) allowing the oxidants to react with the chemiluminescent compounds to emit luminescent light from the test sample;

v) measuring the amount of emitted light over a predetermined period, and vi) correlating extent of infection by comparison of the measured amount of emitted light of the test sample with measured amount of light emitted by a control sample which is treated the same as the test sample for steps i) to v) except that in step i) control antibodies are used which are of the same class as the test antibodies but are non-specific to the sepsis associated markers.

Infectious or septic indicators include antigens of gram-negative bacteria, gram-positive bacteria, virus, fungus or inflammatory mediators such as tumor necrosis factor (TNF), interleukin 1, 6 or 8 and interferons or transforming growth factor $\beta$ (TGF-$\beta$).

In accordance with another aspect of the invention, the test or control sample may be whole blood or white blood cell fractions including neutrophils, lymphocytes and/or monocytes. The addition of zymosan or latex beads and particularly opsonized zymosan or opsonized latex beads enhance the method. The chemiluminescent compound may be, for example, luminol, lucigenin or pholasin. The generation of a differential chemiluminescence response between the test sample using specific antibody and the control using a non-specific antibody of the same isotype is not dependent upon the presence of zymosan or latex but is dependent upon the presence of plasma.

In accordance with another aspect of the invention, monoclonal antibody of the IgM class directed against the lipid A portion of the gram-negative endotoxin is incubated with a patient's blood. A solution of luminol and then opsonized zymosan is added and chemiluminescence is measured for at least 10 to 20 minutes. This is compared to the chemiluminescence of the patient's blood with IgM antibody non-specific to antigens or mediators indicative of infection.

In accordance with another aspect of the invention, a monoclonal antibody of the IgG class directed against Hepatitis A virus is incubated with a patient's blood. A solution of luminol and then opsonized zymosan is added and chemiluminescence is measured for at least 10 to 20 minutes. This is compared to the chemiluminescence of the patient's blood with IgG antibody non-specific to antigens or mediators indicative of infection.

In accordance with another aspect of the invention, a diagnostic kit for use in determining the extent of infection in a patient by detecting the presence of antigen indicative of infection or mediators in response to infection, in a patient's blood derived test sample containing white blood cell fractions comprises:

i) a first container of IgM or IgG antibody specific to antigen or mediators indicative of infection;
  ii) a second container of chemiluminescent compound; and
  iii) a third container of zymosan or latex beads.

The chemiluminescent compound may be selected from the group of compounds consisting of, for example, luminol, lucigenin and pholasin. The antibody may be IgM antibody against gram-negative endotoxin lipid A or IgG antibody against Hepatitis A. The zymosan may or may not be opsonized zymosan, and the latex may or may not be opsonized latex.

According to a further aspect of the invention, a method for detecting the amount of an antigen in a human or animal patient's body fluid test sample in the presence of white blood cells and all complement proteins is provided, which comprises:

i) incubating the test sample with an amount of test antibodies specific to the antigen to form antibody antigen complexes;
  ii) allowing the antibody/antigen complexes to interact with the white blood cells and the complement which results in the production of oxidants;
  iii) introducing to either steps i) or ii) a chemiluminescent compound to the test sample;
  iv) allowing the oxidants to react with the chemiluminescent compounds to emit luminescent light from the test sample;
  v) measuring the amount of emitted light over a predetermined period; and
  vi) correlating the amount of the antigen by comparison of the measured amount of emitted light of the test sample with measured amount of light emitted by a control sample which is treated the same as the test sample for steps i) to v) except that in step i) control antibodies are used which are of the same class as the test antibodies but are non-specific to the antigen.

BRIEF DESCRIPTION OF THE DRAWINGS

Preferred embodiments of the invention are demonstrated with respect to the drawings wherein:

FIG. 3A is a graph illustrating the chemiluminescent response using blood from a patient with severe sepsis syndrome who died 6 hours after the sample was taken, as compared to a control antibody of the same class, isotype and concentration but directed against irrelevant epitopes.

DETAILED DESCRIPTION OF THE INVENTION

Figure 1:
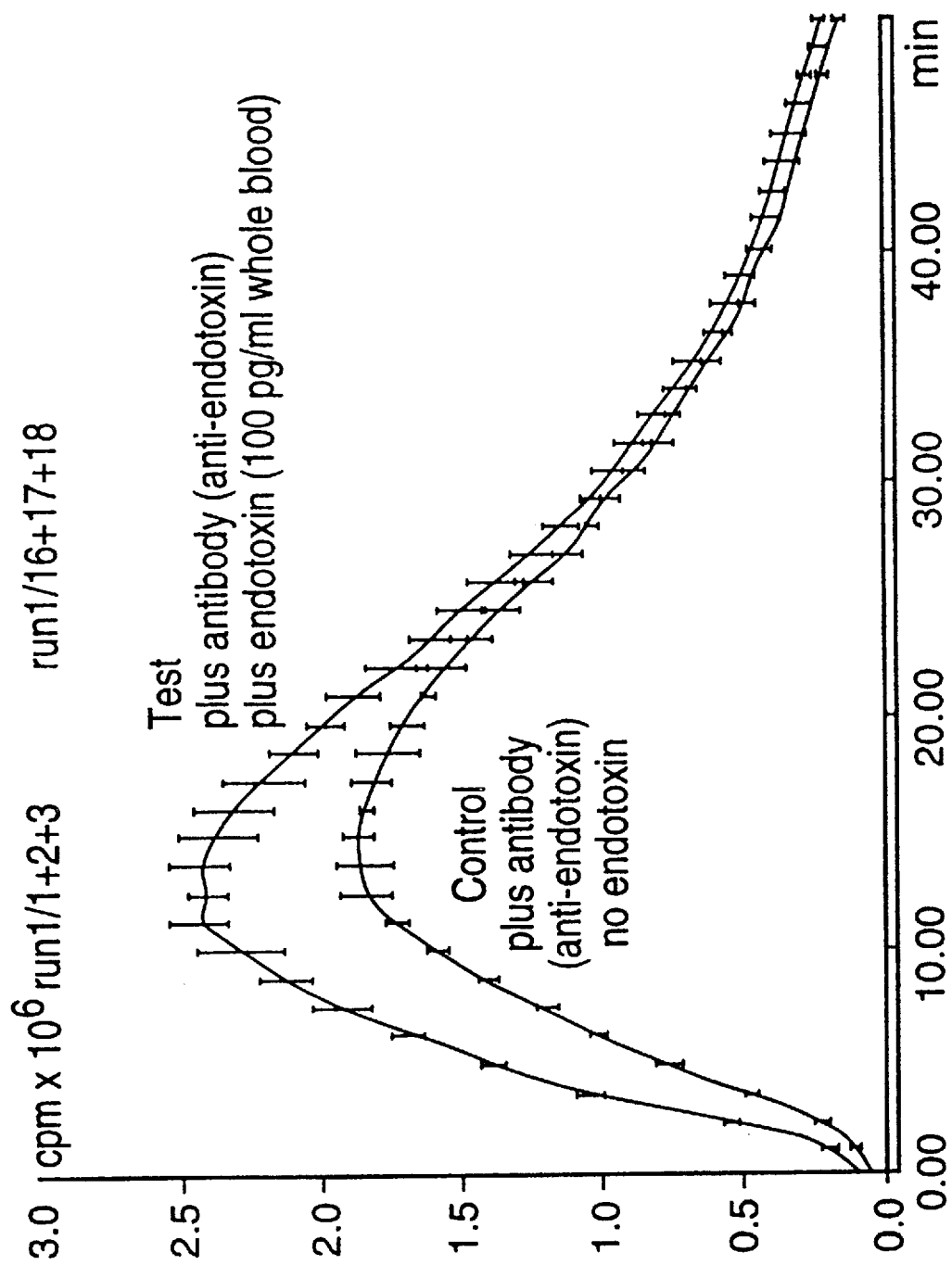
FIG. 1 is a graph illustrating the chemiluminescent response of whole blood with monoclonal antibody and with 100 pg/ml endotoxin and without endotoxin.

The invention is a sensitive, specific and rapid detection method for antigens indicative of infection in whole blood or other body fluids containing white blood cell fractions and all related complement proteins based upon the specificity of antigen-antibody interactions and the high sensitivity of chemiluminescent light emission. The invention provides early diagnostic information for determining the amount of antigens indicative of the extent of sepsis and the amount of any mediators which provide information to indicate the extent or stage of sepsis. Results are obtained in minutes which is a great advantage over the previous time consuming methods of blood culturing for determining sepsis.

The presence of bacteria, viruses or fungi or their related antigenic components in blood is indicative of an infection. In addition, the immune system's reaction to the presence of these foreign antigens by the production of pro-inflammatory mediators such as interleukin-1, (IL-1) TNF and interleukin-6 (IL-6) is also indicative of an infection. The presence and amount of antigens and mediators of sepsis indicates the level or stage of sepsis. For instance, at an early stage of gram-negative sepsis, antibody against gram-negative endotoxin (LPS) in the test of the present invention will detect the presence of LPS at a concentration as low as 5 pg/ml of whole blood. At the next stage, sepsis has progressed and a mediator of sepsis, TNF-α, can be detected and measured using antibody against TNF-α. At stage 3, TNF-α may be present in smaller amounts since it is transitory and another transitory mediator IL-1, may appear. As sepsis progresses further, LPS levels may decrease and TNF-α be absent, but IL-1 may increase and IL-6 may appear. Finally, in a more prolonged case of sepsis, LPS may be present and IL-1 may be at low levels but IL-6 may be at very high levels. Thus, the rapid measurement of antigens and mediators can provide a measure of the patient's severity and duration of sepsis and ensure that the correct treatment is administered. The patient's own antibodies, if produced to an antigen indicative of sepsis, will not appear until 8 to 14 days after exposure to the antigen and thereby do not affect the present invention's antigen detection system.

The present invention measures the amount of antigen and mediators in the patient's blood and provides this information rapidly to determine the patient's level of infection. This rapid test and the staging it provides for a septic patient is critical for the administration of appropriate treatment. If an antigen indicative of sepsis is present in a patient's blood, an antibody specific for the antigen indicative of sepsis can form an antigen/antibody complex at the right concentration of antibody. This is especially effective with monoclonal antibody. This antigen/antibody complex activates complement which in turn causes neutrophils and other white blood cells to produce oxidants. The white blood cells can be stimulated with opsonized zymosan resulting in increased production of oxidants. The oxidants cause an added chemiluminogenic compound, such as, luminol to release light energy. The amount of light emitted over time from a single test can be measured by a luminometer device to indicate the amount of antigen and hence the presence and extent of sepsis. The luminometer may be a Berthold model 953 luminometer which is available from Berthold Instruments Inc. in Austria. The addition of opsonized zymosan enhances the chemiluminescent response. A comparison control sample of the patient's blood is prepared by combining the blood with antibody of the same class non-specific for antigens indicative of sepsis.

The use of chemiluminescence to detect oxidant production is also described in U.S. Pat. No. 5,108,899 to Robert C. Allen. The Allen patent, however, measures inflammation of a patient by comparing the extent of opsonin receptor expression on phagocytes with the maximum inducible opsonin receptor expression. The theory is that the less opsonin receptor expression may be induced, the greater the inflammation. The Allen patent uses agents which bind to phagocytes and stimulate opsonin receptor expression to give a maximum amount of chemiluminescence with zymosan.

In contrast, the present invention adds an antibody specific for an antigen or mediator of sepsis or infection. If an antigen or mediator is present, then antibody/antigen or antibody/mediator complex is formed. The formation of antigen/antibody complexes in blood results in the activation of the classical complement pathway in the case of IgM complexes via C1q with the formation of complement anaphylatoxin and lytic products of C3, C4 and C5. A heat labile element produced during this process is responsible for the activation of white cell oxidant production (see Example XII) which results in the oxidation of luminol with subsequent emission of light. IgG immune complexes may modulate white cell oxidant production and chemiluminescence via a different mechanism which could involve binding to white cell Fcγ receptors and subsequent formation of membrane attack complex followed by cell lysis. Leukocytes do not have Fc receptors for IgM immune complexes. In the present invention, a patient's blood is tested for the level of antigens and mediators which quantities indicate the stage of sepsis. Example X demonstrates that activation of white blood cells by immune complex formation is by a mechanism other than increased opsonin receptor expression. The Allen patent only indicates how much further opsonin receptor expression may be induced, but unlike the present invention, it does not indicate which antigens or mediators are present and at what levels nor does it provide the stage of sepsis.

Although zymosan or latex beads are not a required addition to the test procedure, the measure of immune complexes in the test sample as compared to the control is enhanced by the addition. Zymosan and latex beads enhance the chemiluminescent response by stimulating concerted white cell oxidant production and phagocytosis. The addition of zymosan or latex acts as an amplification process to increase oxidant production but is not obligatory for the recognition of immune complex formation. The enhanced production of white cell oxidants stimulated by IgM immune complexes is not dependent upon increased opsonin receptor expression since the addition of a maximal stimulatory dose of C5a (which upregulates maximal opsonin receptor expression) to the blood during immune complex formation does not significantly affect the ratio of control to specific antibody dependent chemiluminescence when expressed as a light integral or peak count per minute either in the presence or absence of opsonized zymosan (see Example X).

According to an aspect of the invention, a sample of the patient's whole blood may be tested for the indication of sepsis. The sample of whole blood is mixed preferably with a monoclonal antibody, such as, Xomen-E5, produced by Xoma in Palo Alto, Calif., a murine monoclonal IgM pentamer directed against a lipid A component of gram-negative endotoxin. Lipid A is the toxic inner core portion of the lipopolysaccharide (LPS) which is highly conserved and thereby is present on all gram-negative bacteria. The blood, which may contain endotoxin, is incubated with the monoclonal antibody. In parallel, a non-specific control murine antibody of the same isotype is incubated with a sample of the blood for comparison. To the blood-antibody mixture is added luminol solution and then complement activated zymosan or complement opsonized latex beads.

All analyses are preferably carried out in triplicate and the complete assay mixture in polystyrene or glass cuvettes is placed in a thermostated (37° C.) chemiluminometer for repeated multiple readings of light emission intensity. In order to provide a semi-quantitative estimate of the amount of endotoxin in the blood sample, the analysis is conducted, in accordance with one aspect of the invention, using 3 different dilutions of specific and control antibody each of which differ from the next highest concentration by one order of magnitude (i.e., 1:10, 1:100, 1:1000 dilution). The presence of antigen of interest, in this case, gram-negative endotoxin is confirmed by a statistically significant increase in integrated light intensity or reaction slope during the first 10 to 20 minutes of reaction. The three different concentrations of antibody are used to discriminate and semi-quantitate the amount of endotoxin which is present. The principle of the triple concentration approach is based on the observation that maximal stimulation of which cell chemiluminescence in whole blood occurs when antigen-antibody complementarily is optimal for the formation of macromolecular crosslinked complexes or aggregates. In the presence of high concentrations of antigen, a high antibody concentration is required to yield such optimal complementarily. Similarly, at intermediate and low concentrations of antigen less concentrated antibody is required for optimal complementarily and macromolecular aggregate formation. This basic principle has been used for years in Ouchterlony diffusion plates and radial diffusion plates for immunometric quantitation of precipitin reactions. The whole blood chemiluminescent approach provides a semi-quantitative determination of the antigen concentration in question as high, intermediate or low with analogous concentration range (i.e., $\geq 100$ pg/ml, 20–100 pg/ml, $\leq 20$ pg/ml). Thus the maximal stimulation of chemiluminescence will occur for the 1:10 antibody dilution when the antigen level is at $\geq 100$ pg/ml; for the 1:100 antibody dilution when the antigen level is at 20–100 pg/ml; and for the 1:1000 antibody dilution when the antigen level is at $\leq 20$ pg/ml.

A whole blood sample may be used directly in this invention which simplifies the procedure, allowing it to be conducted at the bedside. Diluted whole blood or white blood cell fractions may also be used in this invention. Besides being more time consuming, fractionating procedures may result in loss of subpopulations of neutrophils (Risola, M. and Repo H., APMIS 503:97 (1989)). Using whole blood is much faster, easier and provides the chemiluminescent response above background noise and capture of light energy. An added potential advantage of the utilization of whole blood rather than plasma or serum as the sample and partial reagent, is that it allows the detection of antigens which are cell associated or bound but still expose accessible epitopes. The use of antibodies against such epitopes may allow antibody binding with the receptor or binding sites on cells permitting a positive analytical signal which would not otherwise be detectable in a plasma or serum sample alone.

The antibody against an antigen indicative of sepsis or against a mediator can be of the IgM class. Unlike IgG, IgM does not bind to the Fc receptors on the white blood cells. IgM-antigen complexes trigger a reaction sequence which results in the stimulation of white blood cells oxidant production via a heat labile plasma component. Thus white blood cell activation is dependent upon a classical complement pathway activation which is triggered by the formation of antigen-antibody complexes.

The antibody against an antigen indicative of sepsis or against a mediator can also be of the IgG class. IgG binds to the Fc receptors on the white blood cells and can cause cytolysis. Under these circumstances, there is a decrease in the level of white blood cell activation from the normal level since white blood cells are lysed. This then also provides a semiquantitative measure of the level of antigen present and shows an especially dramatic drop in white blood cell activation with high levels of antigen or mediator.

The chemiluminescent response is measured for at least 10 to 20 minutes to determine the extent of sepsis in comparison to a control. Chemiluminescence may be measured for an hour or longer, but over time the neutrophils appear to be progressively deactivated or their chemiluminescent response is exhausted or an inhibitory luminol metabolite is formed.

Zymosan is a fungal polysaccharide which is optionally used to stimulate phagocytic cells. It is well known that phagocytic cells elicit a maximal phagocytic response when they can ingest particulate matter particularly via receptor-mediated mechanisms. Although untreated zymosan can stimulate the phagocytic response, a much more exaggerated response can be achieved by opsonizing the zymosan first. The process of opsonization for this invention involves the binding of IgG's and complement factors iC3b and C3b to the zymosan. This process allows the opsonized zymosan to bind to three different classes of receptors on the phagocytic cells. IgG's bind to specific Fc receptors, C3b coated particles bind to $CR_1$ receptors and iC3b-coated particles bind to the CR3 receptor. Non-opsonized zymosan binds only to a subsite of the CD11b/CD18 integrin receptor which is different from the iC3b-$CR_3$ binding site. Due to its multiplicity of binding sites, opsonized zymosan triggers a much more vigorous respiratory response in phagocytic cells than a comparable concentration of non-opsonized zymosan. In this invention opsonized zymosan is used to maximally elicit the oxidative response of the white blood cells. Opsonized zymosan white blood cell activation is dependent upon the concentration of $CR_1$ and $CR_3$ receptors on the surface of the phagocytes. The best results use complement opsonized zymosan (minimal IgG), however any type of opsonized zymosan may be used, for example, IgG opsonized or complement and immunoglobulin opsonized. Complement opsonized latex beads can be used to maximally elicit the oxidative response of the white blood cells.

The preferred aspect of this invention uses a small volume of undiluted whole blood (20 $\mu$l or 50 $\mu$l) heparinized (<2 U/ml) or EDTA anticoagulated and kept at room temperature. The blood sample is incubated with an equal volume of antibody (0.2, 0.02 and 0.002 mg/ml) at 37° C. for five to ten minutes. After incubation, 200 $\mu$l of 40 $\mu$M luminol solution is added followed by 50 $\mu$l of complement opsonized zymosan, (2.5–3.0×$10^9$ particles ml). The sample is read in a thermostated (37° C.) luminometer.

In another aspect of this invention, whole blood is first combined with luminol solution and then antibody is added and the mixture incubated at 37° C. for five to ten minutes. Zymosan may then be added.

The examples describe alternatives to these aspects, such as varying the order in which to add the reagents, varying blood dilutions, and omitting zymosan. However, the above aspects provide a better evaluation of the presence and degree of sepsis. Modifications of these protocols will still be within the scope of the invention. The whole blood sample may instead be a sub-fraction of white blood cells, such as neutrophils or lymphocytes or monocytes. A chemiluminescent compound other than luminol may be used, such as, lucigenin or pholasin.

The phenomenon of chemiluminescence resulting from the production of neutrophil oxidants is described by Allen, R. C. Methods in Enzymology 133:449 (1986) using the acyl azide dye luminol as a light emitting agent. This technique permits the sensitive measurement of neutrophil respiratory burst activation using small numbers of polymorphs or later, even white cells in whole blood. The exact mechanism of light emission from the dye luminol has not been elucidated to date but is thought to involve a chlorinated intermediate produced upon reaction of the dye with hypochlorite at neutral pH. An excited state proceeding through an "activated aldehyde" intermediate is thought to relax to ground state by emission of light at about 450 nm. The quantum yield of this process is of the order of 1%, that is, only 1% of the energy of reaction is emitted as light. The major oxidant produced by white cells, which is thought in accordance with this invention to excite luminol, has been shown to be HOCl, although a superoxide anion which is also an oxidant produced by white cells can also excite the dye predominantly at alkaline pH. The primacy of HOCl as the oxidant species which triggers luminol dependent chemiluminescence has been confirmed in whole blood studies using sodium azide as an inhibitor of myeloperoxidase (Allen, R. C. *Methods of Enzymology* 133:449 (1986). Under these conditions greater that 95% of the chemiluminescent light emission is blocked. Other chemiluminescent dyes which produce light as a result of neutrophil oxidant production have also been identified including lucigenin and pholasin.

Experiments conducted with azide as an inhibitor of myeloperoxidase (Pauksens, K. et al. *Scand. J. Infect. Dis.* 21:277 (1989)) as well as other studies using purified human neutrophils, suggest that polymorphs are the major contributors of oxidants and myeloperoxidase enzyme in whole blood chemiluminescence studies which employ luminol as the primary lumiphor. The major stimulation of whole blood respiratory burst activity occurs when the white cells, particularly the polymorphs, are presented with a phagocytizable particle (1–2.5 micron in diameter) which is opsonized with complement or immunoglobulin products. Phagocyte contact with complement or immunoglobulin opsonized foreign bodies such as microbes results in a programmed sequence of events. This includes:

a) phagocyte recognition of the opsonized material by the opsonin-specific receptors $CR_1$, $CR_3$ (CD11b/CD18) and Fc receptors, b) engulfment or phagocytosis of the foreign body if it is of appropriate dimensions, and c) activation of white cell redox metabolism.

The respiratory burst activity provides reducing equivalents for univalent reduction of oxygen via the hexose monophosphate shunt in the form of NADPH which is used as an electron source for the membrane-associated oxidase complex which generates superoxide anion $O_2$ into the phagolysosome or the extracellular space. This primary oxidant production in concert with the degranulation of azurophil granules results in the formation of more powerful oxidants such as HOCl which act in concert with neutrophil proteases to kill bacteria and inactivate viral particles.

Allen has proposed in his aforementioned U.S. patent, the use of whole blood chemiluminescence elicited by complement or immunoglobulin-opsonized zymosan as a technique to evaluate the degree of white cell, and particularly polymorph activation, in patients who have activated immune responses. He has devised a kinetic method for measuring neutrophil opsonin receptor expression which is based upon stimulation of whole blood with saturating concentrations of opsonized zymosan. The zymosan maximally stimulates the expressed $CR_1$ and $CR_3$ receptors resulting in oxidative burst activity and degranulation which in the presence of luminol transduces the oxidant burst into light emission which can be integrated and quantitated. In order to maximally induce all available opsonin receptor expression (both ambient and latent) a separate analysis is conducted with a maximum stimulatory dose of C5a. The ratio of ambient to maximally induced chemiluminescence in the presence of complement anaphylatoxin C5a provides an index of inflammatory status which is independent of white cell or polymorph concentration. It has been shown that the instantaneous level of opsonin receptor concentration in a patient's white cell cohort is dependent upon the concentration of pro-inflammatory mediators (PAF, $LTB_4$, C5a, etc.) which are in contact with the white cells at any one time. The measurement of opsonin receptor reserve, therefore, provides a rapid functional assessment of inflammatory status which can be used in a prognostic manner. The Allen method does not measure the presence of antigens indicative of sepsis or mediators in the blood. The present invention does measure the presence of such antigens or mediators by the formation of immune complexes using exogenously added antibody. The Allen method instead measures the degree of phagocyte activation and oxidant production via opsonin receptor expression. The present invention uses the white cell excitation to measure the presence of antigens indicative of sepsis.

The use of chemiluminescence to detect superoxide anion formation triggered by lipoteichoic acid-antibody interaction has only been previously described in the context of purified neutrophils which were pre-coated with lipoteichoic acid and subsequently challenged with antibodies against lipoteichoic acid (Ginsberg, I., et al. *Inflammation* 12:525 (1988)). Lipoteichoic acid is known to non-specifically adhere to neutrophils via its lipid moiety. The addition of antibodies against lipoteichoic acid triggered a small respiratory burst activity, which was shown to be dependent upon prior coating of the neutrophils with lipoteichoic acid and subsequent crosslinking or agglutination of neutrophils, which was induced by antibody acting as a bridging ligand between lipoteichoic acid on the surface of one neutrophil binding to the Fab portion of the antibody, followed by binding of adjacent neutrophils via Fc receptors. In these studies antibodies of the IgG class were used. The authors of this study did not recognize the fact that luminol detected primarily HOCl production in their purified neutrophil preparations and did not comment on the obvious differences in the kinetics of oxidant production observed in the presence of luminol or cytochrome "c" as detectors of oxidant production.

The present invention's analytical approach is based upon a different mechanism of signal amplification. In one aspect of the invention, the antibodies of the murine monoclonal IgM class are directed against gram-negative endotoxin lipid A (a component of lipopolysaccharide (LPS)). These antibodies do not have complementary Fc receptors on neutrophils or any other white cell subtype (Unkeless, J. C., Boros, P., Fein, M., *Inflammation, Basic Principles and Clinical Correlates,* 2nd Ed., 497–510; Gallin, J. I., Goldstein, R., Synderman, R., Editors Raven Press, N.Y. (1992). The detection of fluid phase antigen-antibody complexes is based on their ability to fix complement and stimulate white cell oxidant production compared to a control sample containing an irrelevant isotype-matched antibody. The subsequent stimulation of the neutrophils with a non-rate limiting dose of zymosan allows an enhanced signal to be generated by maximal stimulation of phagocytosis. In the absence of antigen, no such enhanced response is elicited. Complement opsonized zymosan is added to maximize the phagocytic response of neutrophils.

For the purpose of analyzing patient samples, which may or may not contain antigen, a control comparison sample is co-analyzed with an identical subclass and concentration of antibody which is directed against an irrelevant epitope not found in human blood. By comparing the chemiluminescent response in the control tube with irrelevant antibody to the tube containing specific antibody against the antigen of interest, it is possible to obtain a semi-quantitative estimate of the concentration of antigen, after an assay period of 20 minutes or less. The presence of antigen is confirmed by an enhanced chemiluminescence response during the early assay period in the tubes containing specific antibody. One of the examples confirms that *E. coli* bacteria added to the blood test sample had no detectable effect on neutrophil chemiluminescence during the time course (<60 minutes) of the observed assay in the absence of antibody against LPS. Endotoxin could eventually cause neutrophil activation of the antigen/antibody complexes.

In another aspect of this invention, antibodies of the murine monoclonal IgG class are directed against Hepatitis A virus. These antibodies do have complementary Fc receptors on white blood cells. The binding of the antigen/antibody complex on the Fc receptors may cause the white blood cells to lyse thus attenuating their oxidant burst. The attenuation of white blood cell oxidative metabolism at an appropriate antibody concentration due to cell lysis or inhibition of respiratory burst activity may be used to signal the presence of Hepatitis A virus. Thus any IgM/antigen complexes will activate complement and cause increased oxidant production of white blood cells, while IgG/antigen complexes will cause them to lyse, thus reducing oxidant production from baseline levels.

A unique feature of the present invention is that the patient's own finely tuned immune recognitive systems are used to provide the analytical signal. This approach is unique because the patients blood is pre-incubated with either control or target antibody for five to ten minutes prior to the addition of luminol and opsonized zymosan and then the chemiluminescent light emission signal is measured for a period of 10 to 20 minutes. A comparison of calculated slopes or integrated light intensity of the response to control or specific antibody allows a decision to be made regarding the presence or absence of the antigen. In order to guarantee optimal reaction conditions for antibody/antigen complementarity, three concentrations of antibody can be used, each with a matched control. This approach allows rapid and extremely sensitive detection of gram-negative endotoxin at a detection limit which is to comparable to or lower than many conventional Limulus Amoebocyte Lysate (LAL) assays which require extensive blood sample pretreatment and are much more labor intensive and prone to environmental contamination. It also uses whole blood rather than serum or plasma. The results of the present invention's CL (chemiluminescence) method are compared favorably to the LAL assay method in Example VIII. A preferred embodiment of process steps of this invention is described in Example IX and illustrated by FIG. 4.

EXAMPLES

Example I
Verification of the Antibody (Xomen-E5) Binding to Gram-Negative Endotoxin as Assessed by Turbidimetric Assay.

Murine monoclonal antibody (Xomen-E5, stock concentration 2 mg/ml supplied in sterile pyrogen free saline) against gram-negative endotoxin was diluted 10 to 10,000 fold in sterile, pyrogen free Hanks Balanced Salt solution (HBSS) at 10 fold increments. Solid polyethylene glycol 6000 was added to the antibody dilutions to give a final concentration of 6% w/v. The purified gram-negative endotoxin (*E. coli* serotype 055:B5, grade V, Sigma St. Louis, Miss.) was dissolved in HBSS at concentrations of 100, 10, 1 and 0.1 µg/ml (w/v). These two solutions were placed in a Cobas Fara centrifugal chemistry analyzer (Roche Diagnostics, Hoffman La Roche, Miss., Ont.) and equivalent 100 µl volumes were pipetted by the analyzer into cuvettes and optical density measured repeatedly at 340 nm at 30 second intervals for a total period of 5 minutes (Table 1).

To confirm that the monoclonal antibody reacts with the endotoxin, a turbidimetric antigen-antibody binding analysis was conducted. Table 1 summarizes the turbidimetric antigen-antibody interaction of the monoclonal murine IgM antibody directed against the Lipid A epitope of gram-negative endotoxin with purified *E. coli* gram-negative endotoxin (LPS). As demonstrated in Table 1, it is evident that under the conditions of this assay, at an antibody concentration of 2 µg/ml, a dose-response relationship is established against increasing concentrations of LPS (from 1 to 100 µg/ml). This experiment confirms the ability of the antibody to recognize LPS and bind to it to form insoluble antigen-antibody complexes at appropriate concentrations of each reactant which yield optimum complementarily for the precipitin reaction. These results provide, therefore, direct evidence that the antibody chosen for subsequent assay development is capable of recognizing the antigen of interest.

Example II
Effect of Antibody Concentration on the In Vitro Chemiluminescent Response of Whole Blood Containing Gram-negative Endotoxin Whole blood was collected from the antecubital vein of a healthy volunteer into an equal volume of HBSS containing sodium heparin at a final concentration of 2 units/ml. The following solutions were then added to chemiluminescence cuvettes:

200 µl HBSS containing a saturating concentration of luminol (approximately 40 µM), (This solution of will be called luminol solution), 100 µl of Heparinized Whole Blood (Diluted 10 fold with HBSS), 30 µl of antibody solution (final concentration in the total reaction mixture ranging from 100 µg/ml in 10 fold dilutions).

All reaction mixtures were assayed in triplicate. This reaction mixture was temperature equilibrated for 5 minutes at 37° C. in the reaction chamber of a Berthold model 953 autolumat luminometer and 50 µl of complement opsonized zymosan (2.5–3.0×10$^9$ particles/ml) pre-warmed at 37° C. was added to each cuvette. The samples were then read repetitively for a period of 60 minutes in the luminometer at a constant temperature of 37° C. Assays were organized so that every 6 cuvettes contained the same concentration of antibody but only the last three cuvettes of the six contained 1000 pg/ml of endotoxin.

The data in Table 2 illustrate the chemiluminescent response to endotoxin at varying concentrations of anti-LPS antibody. Each group of six cuvettes contains the same concentration of antibody ranging from 100 µg/ml to 0.01 µg/ml in 10 fold increments. The last three tubes in each group contain blood which was supplemented with endotoxin to a concentration of 1 ng/ml. The integrals of the cumulative light intensity are used to determine whether a significant difference exists between triplicate tubes with and without endotoxin at any particular antibody concentration. As demonstrated in Table 2, the highest concentration of antibody yielded a suppression in chemiluminescence when endotoxin was present and the only other antibody concentration which yielded a differential response was the lowest concentration of 0.01 µg/ml. In this group the presence of gram-negative endotoxin yielded an enhancement of chemiluminescence. For the purposes of assay development, an augmentation of chemiluminescence (CL) is preferable since it is more likely to span a broader range of responses to varying concentrations of endotoxin and the lower requirement for antibody would decrease the cost of the assay. The suppression of the CL response at high concentrations of antibody may be due to destruction of neutrophils bound with endotoxin-anti-endotoxin antibody complexes due to complement-mediated lysis of the cells or the inhibition of zymosan activation due to blockade of opsonin receptors by antigen-antibody-complement complexes.

Example III

Chemiluminescent Response of Whole Blood In Vitro With and Without Gram-negative Endotoxin, and with Monoclonal Antibody Against Endotoxin.

One milliliter of whole blood was mixed with endotoxin to yield a final concentration of 1 ng/ml and a duplicate aliquot was mixed with an equivalent volume of carrier (50 µl HBSS). Chemiluminescence cuvettes were then filled in triplicate with 200 µl of luminol solution and 100 µl of blood with and without endotoxin. This blood was pre-diluted ten fold with heparinized HBSS prior to addition to the chemiluminescence cuvettes. To these cuvettes a solution of opsonized zymosan was added (50 µl) along with 25 µl of HBSS. Chemiluminescence was then measured for 60 minutes (Table 3A).

In a parallel series of experiments the same tubes were prepared as above except that tubes were filled with 25 µl of HBSS containing monoclonal antibody against gram-negative endotoxin (final concentration of antibody 1.3 µg/ml) (Table 3b). Example III was designed to examine whether endotoxin alone had any effects on CL in the absence of antibody under the conditions of the assay. At a dose of 1000 pg/ml of whole blood the endotoxin had no effect on the chemiluminescence response. In Table 3A none of the samples contained antibody. As indicated in Table 3B the addition of antibody to a final assay concentration of 1.3 µg/ml had no effect on the shape or magnitude of the CL response in the absence of endotoxin. The presence of endotoxin, however caused an augmentation of the CL response both in terms of increased CL maximum, and increased initial acceleration slope observed during the first 15 minutes of the reaction. These results confirmed the observation that the presence of antigen-antibody complexes could be used to enhance zymosan activated whole blood chemiluminescence and hence detect whether LPS was present in whole blood.

Example IV

Optimization of Chemiluminescent Response of Two Different Endotoxin Concentrations (100 pg/ml and 1000 pg/ml) by Varying the Antibody Concentration Three 1 ml samples of whole blood anticoagulated with EDTA collected from one donor were mixed with 10 µl of HBSS. One of the 10 µl aliquots of HBSS contained 100 pg of endotoxin and the other 10 µl aliquot contained 1000 pg of endotoxin. Each sample either with or without endotoxin was then diluted tenfold with HBSS containing 2 U/L of sodium heparin. The following assay protocol was then used: 200 µl of luminol solution, 100 µl of 10x diluted blood, 25 µl of monoclonal antibody against endotoxin and 50 µl of complement opsonized zymosan. The final concentration of monoclonal antibody in the reaction mixture was varied from 0.2 µg/ml to 0.0025 µg/ml in dilution increments of 3 fold. All assays were analyzed in triplicate and the reactions were initiated by the addition of opsonized zymosan to the reaction mixture. The chemiluminescent response was monitored for 50 minutes at 37° C. Chemiluminescent curve integrals were taken from the time of zymosan addition until 5 minutes of the initial acceleration phase of the reaction for comparison of responses. All integrals were compared to the parallel control containing an equivalent concentration of monoclonal antibody but no endotoxin (Table 4).

The possibility that one antibody concentration could span a range of CL response from 0 to 1000 pg/ml of endotoxin was investigated in Example IV. The assay results are summarized in Table 4. After careful inspection of the data obtained over a 50 minute assay period it was observed that the best signal to noise ratio was achieved by considering CL curve integrals over the first five minute acceleration phase of the reaction. This data is tabulated in the "Integral" column of Table 4. The starting antibody dilution in this experiment was 0.2 µg/ml. All subsequent dilutions of antibody were made in threefold steps. It is clear from this data that the maximal response ratio between control cuvettes with no endotoxin and cuvettes containing blood with an endotoxin concentration of 100 pg/ml was achieved at the highest concentration of antibody tested, namely 0.2 µg/ml. The response ratio at this concentration was 2.1. At an LPS concentration of 1000 pg/ml, the maximal response ratio was achieved at an antibody concentration, of 0.007 µg/ml. At this antibody concentration, the response ratio for the 1000 pg/ml standard was 1.7.

These experiments highlight the fact that no one single antibody concentration can give a significant signal to baseline response at both these concentrations of endotoxin. The preferred systematic approach with regard to patient samples is to assay for the presence of endotoxin at several concentrations of antibody in order to maximize the probability of detection over a wide possible range of endotoxin concentrations which are likely to occur physiologically in patients. These rules also highlight the observation that the amount of antibody used in the assay modulated the baseline chemiluminescent response in the absence of endotoxin suggesting that any patient-based assay protocol should employ an equivalent concentration of an irrelevant antibody which would give a CL response indistinguishable from the specific antibody in the absence of the antigen of interest.

FIG. 1 graphically presents the CL data obtained from the reaction mixtures which gave the largest response ratio for endotoxin at a concentration of 100 pg/ml of whole blood. The plotted data emphasizes the difference in the initial slope of the reactions and in the CL maxima. An adequate differentiation of the signals was clearly evidenced after only 5 minutes of reaction emphasizing the rapid diagnostic potential of the assay. The standard chemiluminometer measures emitted luminescent light by use of the standard type of electronic photo counter. Periodically as plotted along the X-axis in minutes, the light emission is measured based upon the photon counts per minute (cpm). The cpm value is then plotted on the Y-axis whereby over time the receptive curves are developed. In summary, the presence of endotoxin in the sample results in a steeper reaction slope during the acceleration phase of the reaction and a higher CL maximum light emission. In many samples, the time to reach CL maximum is shortened by the presence of endotoxin.

Example V

Chemiluminescent Response of Whole Blood Containing In Vitro Added LPS (Gram-negative Endotoxin) with Addition of Antibodies to LPS but no Zymosan (i.e., Chemiluminescent Response in the Absence of an Opsonin Receptor Agonist)

A) These experiments were conducted using the following reaction mixture: 200 µl luminol solution, 100 µl of whole blood diluted 10x with heparinized HBSS containing an original undiluted endotoxin concentration of 0, 10, 50 and 100 pg/ml and 50 µl of monoclonal murine anti-LPS antibody (concentration 0.2 mg/ml final concentration in the assay mixture 28.5 µg/ml). The chemiluminescent reaction was initiated by luminometer-controlled injection of the diluted blood into the cuvettes and subsequent reading of chemiluminescence (CL) intensity after a 0.5 second delay (Table 5c).

B) In a separate experiment, the CL response of anti-endotoxin and control non-specific murine myeloma IgM to 1 ng/ml of endotoxin in whole blood was evaluated using equivalent concentrations of antibody (28.5 µg/ml) using the same experimental protocol as in part A (Table 5a and b).

It has been well established that human neutrophils do not have Fc receptors which recognize IgM of human or murine origin. The source of the CL signal which is observed in the presence of zymosan could not be due to a direct interaction of antigen-antibody complexes with neutrophil Fc receptors, resulting in a cross linking of Fc receptors which is known to stimulate respiratory burst activity. In order to investigate the possible mechanism of neutrophil chemiluminescence stimulation observed with IgM antibodies of both specific and non-specific epitope recognition, the CL signal generation in the absence of exogenous zymosan activation which maximally recruits available surface expressed opsonin receptors was examined. As illustrated in Table 5, addition of equivalent concentrations of the non-specific control antibody and the anti-LPS antibody in the absence of endotoxin resulted in no significant activation of white cell population. Addition of endotoxin, however, resulted in a biphasic increase in CL response in the samples containing anti-LPS antibody only. The excitation of CL in whole blood as a result of antigen-antibody complexes of the IgM class implies that the augmented CL response is triggered by factors other than Fc receptor occupancy, such as release of complement products or other proinflammatory molecules generated as a consequence of specific antigen-antibody complexes. Another feature of these results is the difference in the magnitude of the CL signal generated by antigen-antibody complexes in the absence of zymosan. The intensity of the CL signal with zymosan is approximately 50–100 times higher than without. For this reason opsonized zymosan is used in this invention to increase the magnitude of the response and improve signal to noise characteristics. As indicated in Table 5, Panel C, there was a dose-response relationship between endotoxin concentration and the magnitude of CL integral. The biphasic nature of the CL response implies that the early peak which occurs in the presence of LPS is due to intracellular oxidant production and the later progressive rise is due to extracellular oxidant release which is temporally later in the sequence of cell activation. The general assay protocol may be used without the inclusion of opsonized zymosan to prime and excite a maximal respiratory burst activity.

Example VI
Effect of Pre-Incubation Time with Monoclonal Antibody on Chemiluminescence Response in the Presence of Exogenously Added LPS In this experiment, the concentration of blood used in the assay mixture was altered in order to try to increase assay sensitivity. Rather than diluting the blood 10× with heparinized HBSS prior to assay, the blood was diluted only 2 fold with the same buffer. In this experimental series the luminol volume was decreased to 100 µl and 100 µl of blood (diluted 2×) was used which had an original endotoxin concentration of 10 pg/ml, or no exogenously added endotoxin. Fifty microliters of monoclonal antibody was used in the assay protocol (concentration of antibody ranged from 0.2 mg/ml to 2 ng/ml in the 50 µl aliquot).

Figure 2A:
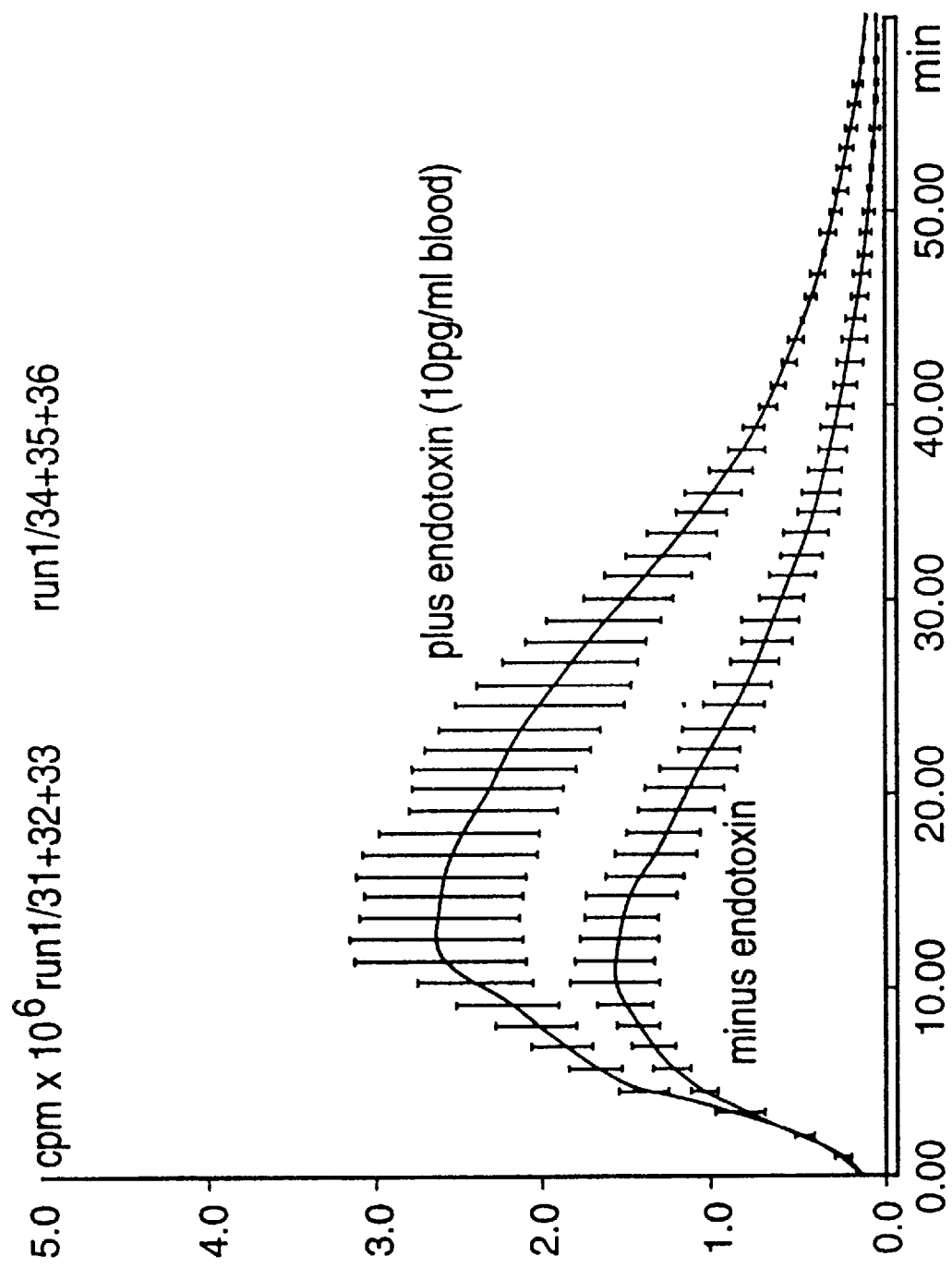
FIG. 2A is a graph illustrating the chemiluminescent response with 5 minute pre-incubation with monoclonal antibody with and without 10 pg/ml endotoxins.

A) In one series of experiments, the blood (diluted 2×) was pre-incubated with 50 µl of antibody solution for 5 minutes at 37° C. prior to addition of luminol solution and 50 µl of complement opsonized zymosan to initiate chemiluminescence (FIG. 2A, Table 6a). This assay protocol is the preferred embodiment of the invention.

Figure 2B:
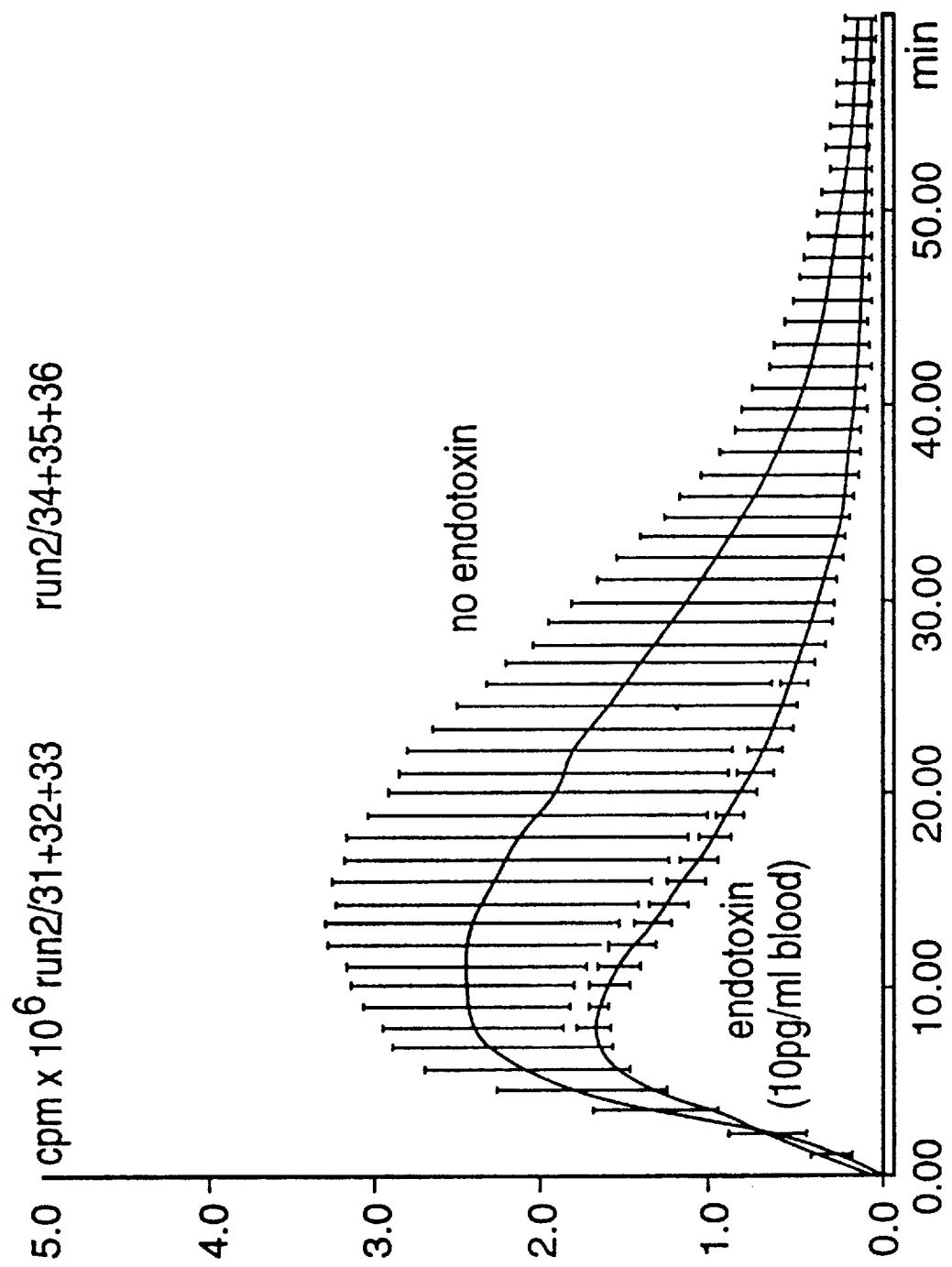
FIG. 2B is a graph as in FIG. 2A except that the incubation period with antibody is 60 minutes.

B) In a separate parallel series of experiments, the pre-incubation period with antibody was extended to 60 minutes prior to the addition of luminol solution and zymosan. (FIG. 2B, Table 6b). In both experimental series A and B the CL response was monitored for 60 minutes after the addition of zymosan.

It is an advantage of this invention to diagnose low levels of endotoxin as it is easier to treat early sepsis. The CL response to low doses of endotoxin (10 pg/ml of whole blood) was optimized by increasing the volume fraction of blood in the total reaction mixture and also diluting the whole blood only 1:1 rather than 1:9 as in previous assays. These modifications are designed to push the limits of sensitivity high enough to allow very early detection of endotoxemia in order to attempt to detect gram-negative endotoxin in the blood well before catastrophic activation of the immune response is triggered. As indicated in Table 6a, which summarizes the response to LPS with a short pre-incubation of antibody for 5 minutes, the best response ratio was achieved at an antibody concentration of 200 µg/ml which resulted in an almost 2 fold signal enhancement in the presence of 10 pg/ml of endotoxin. Table 6b summarizes a parallel experiment except that samples were pre-incubated with anti-LPS antibody for 60 minutes prior to the addition of opsonized zymosan. In this case pre-incubation with antibody for 1 hour resulted in a decreased CL response in the endotoxin-containing samples with an antibody concentration of 200 µg/ml. This response suggests that prolonged incubation times may have allowed complement activation to proceed to the formation of the membrane attack complex with lysis of neutrophils. Alternatively, the prolonged incubation times may have allowed the opsonized antigen-antibody complexes to bind to $CR_1$ and $CR_3$ receptors on the neutrophils and block the binding of complement opsonized zymosan to these opsonin receptors. FIG. 2A exemplifies the maximal stimulatory effect observed with the short pre-incubation period. FIG. 2B graphically illustrates the inhibitory effect which occurs with identical antibody concentrations but a long pre-incubation time. The short pre-incubation strategy is preferred since it allows signal amplification rather than a CL suppression in the presence of LPS.

Example VII
Dose-Response of Whole Blood Chemiluminescence Reaction to Increasing Concentrations of Endotoxin at a Fixed Concentration of Antibody Utilizing Control (Non-Specific Murine Myeloma IgM) and Anti-LPS Murine IgM Antibody Whole blood collected in EDTA vacutainer tubes was supplemented with LPS at concentrations of 0, 5, 50 and 500 pg/ml. One hundred microliters of undiluted blood was mixed with 50 µl of antibody solution containing either non-specific control antibody or anti-endotoxin antibody at a concentration of 0.2 mg/ml and with 200 µl of luminol solution. The reaction mixtures were pre-incubated with antibodies for 5 minutes at 37° C. and then 50 µl of opsonized zymosan was added and the CL response monitored for a period of 60 minutes (Table 7a, b, c and d).

Example VII examines whether a differential CL dose-response could be achieved under assay conditions which would readily detect small concentrations of endotoxin. As indicated in Table 7, there was not a significant difference in the initial velocities of the CL response in the absence of endotoxin, the mean slope for the linear portion of the control curves was $0.113 \times 10^6$ cpm/minute, for the anti-LPS curves the mean slope was $0.133 \times 10^6$ cpm/minute. As shown in Table 7, at a dose of LPS of 5 pg/ml of whole blood, the mean slope for the anti-LPS antibody curves was 0.159×10⁶ cpm/minute, while the slope for the control antibodies remained at 0.114×10⁶ cpm/minute. In Table 7, the mean slope for the endotoxin containing curves was 0.226×10⁶ cpm/minute at an LPS dose of 50 pg/ml of whole blood and 0.226×10⁶ cpm/minute at an LPS dose of 500 pg/ml of whole blood. The linear portion of the CL response curve for the control antibody curves remained constant at 0.116 to 0.113×10⁶ cpm/minute. These results demonstrate that a dose-response relationship can be generated for concentrations of LPS ranging from 5–500 pg/ml. Such a response could allow quantitative or semiquantitative detection of endotoxin in patient samples. With this assay protocol, the utility of the CL assay was examined in ICU patients who had clinical evidence of sepsis or risk of sepsis and patients with no clinical evidence or at low risk of sepsis.

Figure 3B:
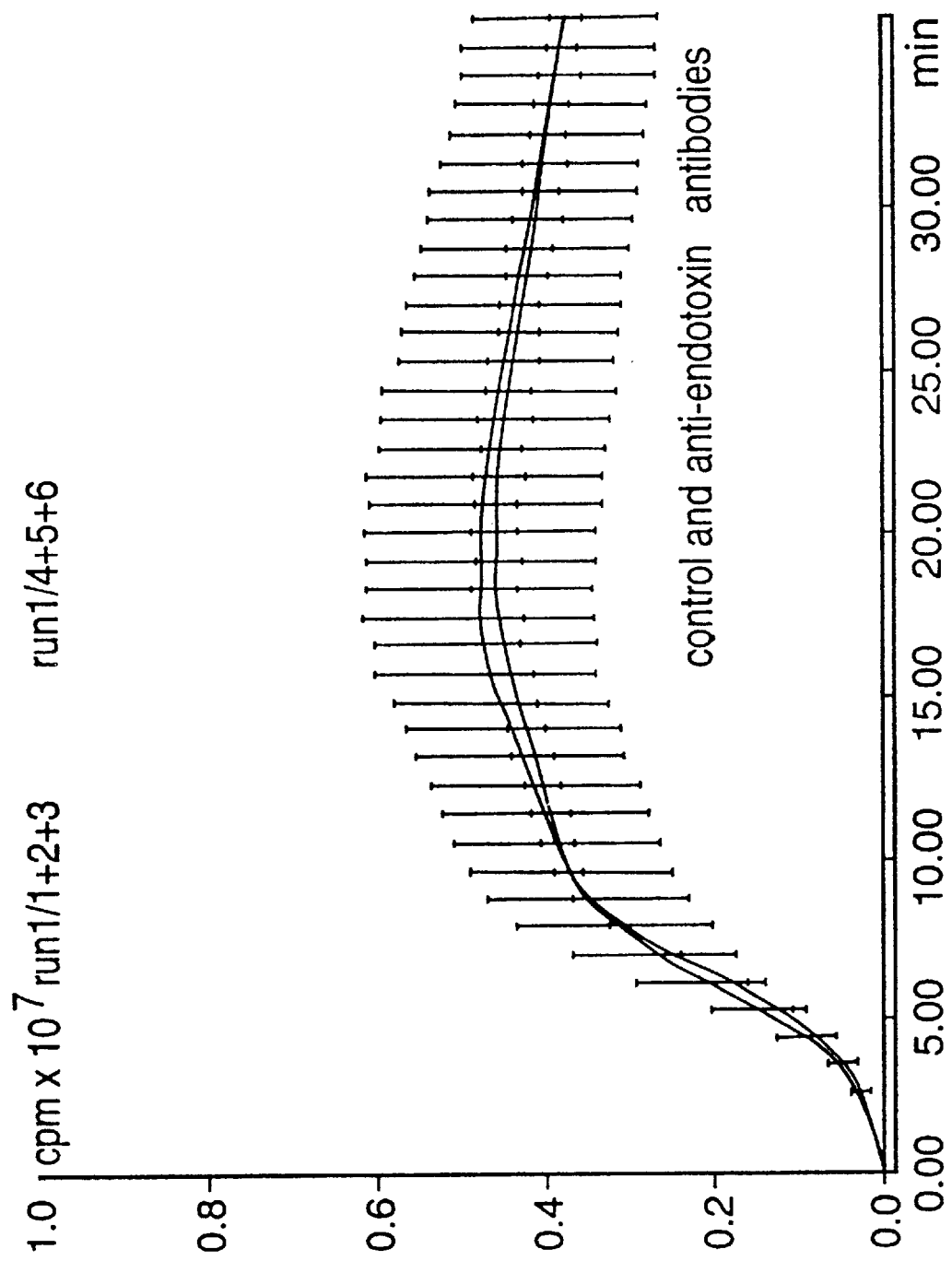
FIG. 3B uses blood from a healthy ambulatory volunteer.
Figure 3C:
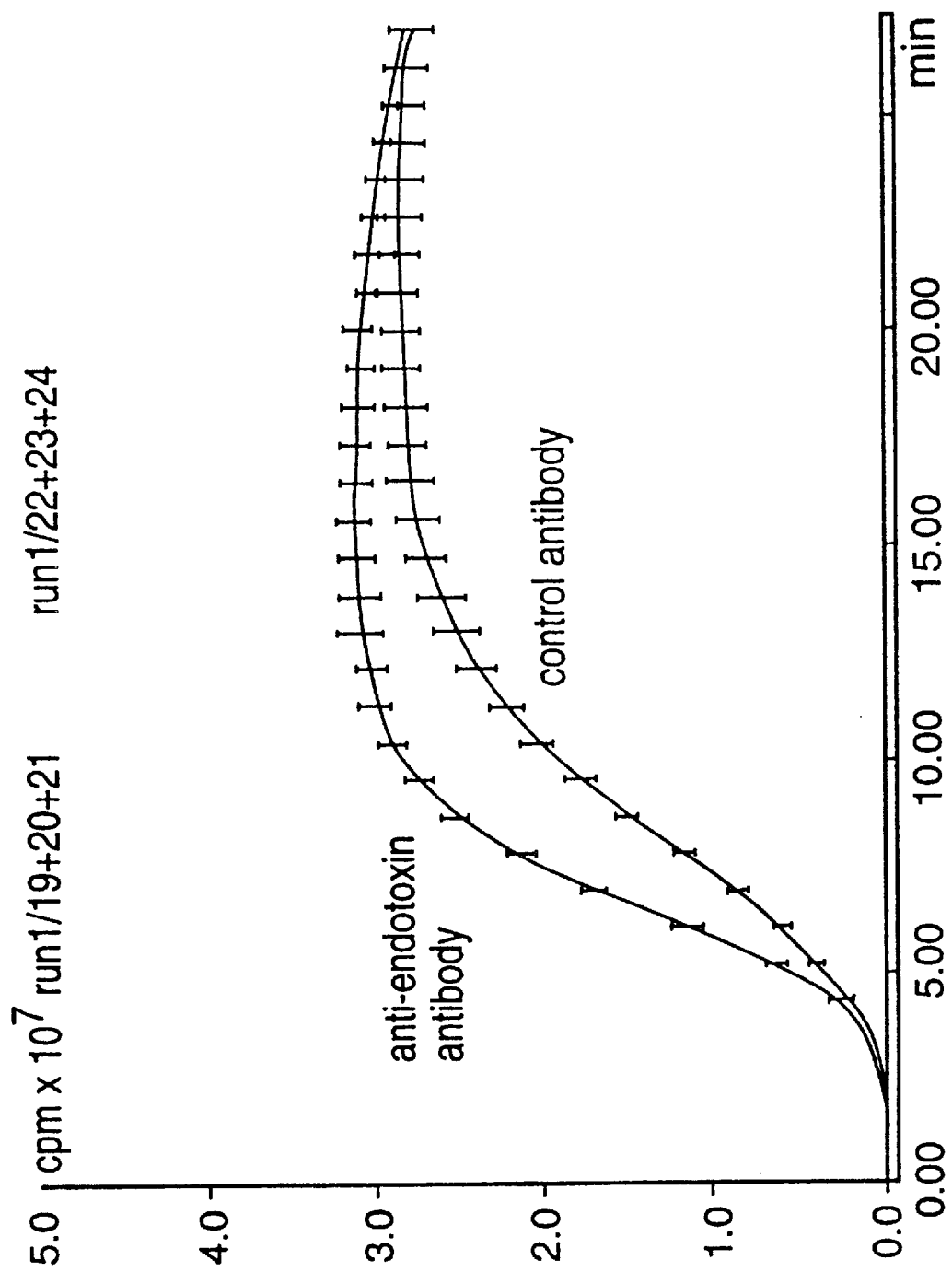
FIG. 3C uses blood from a patient with chronic sepsis.
Figure 3D:
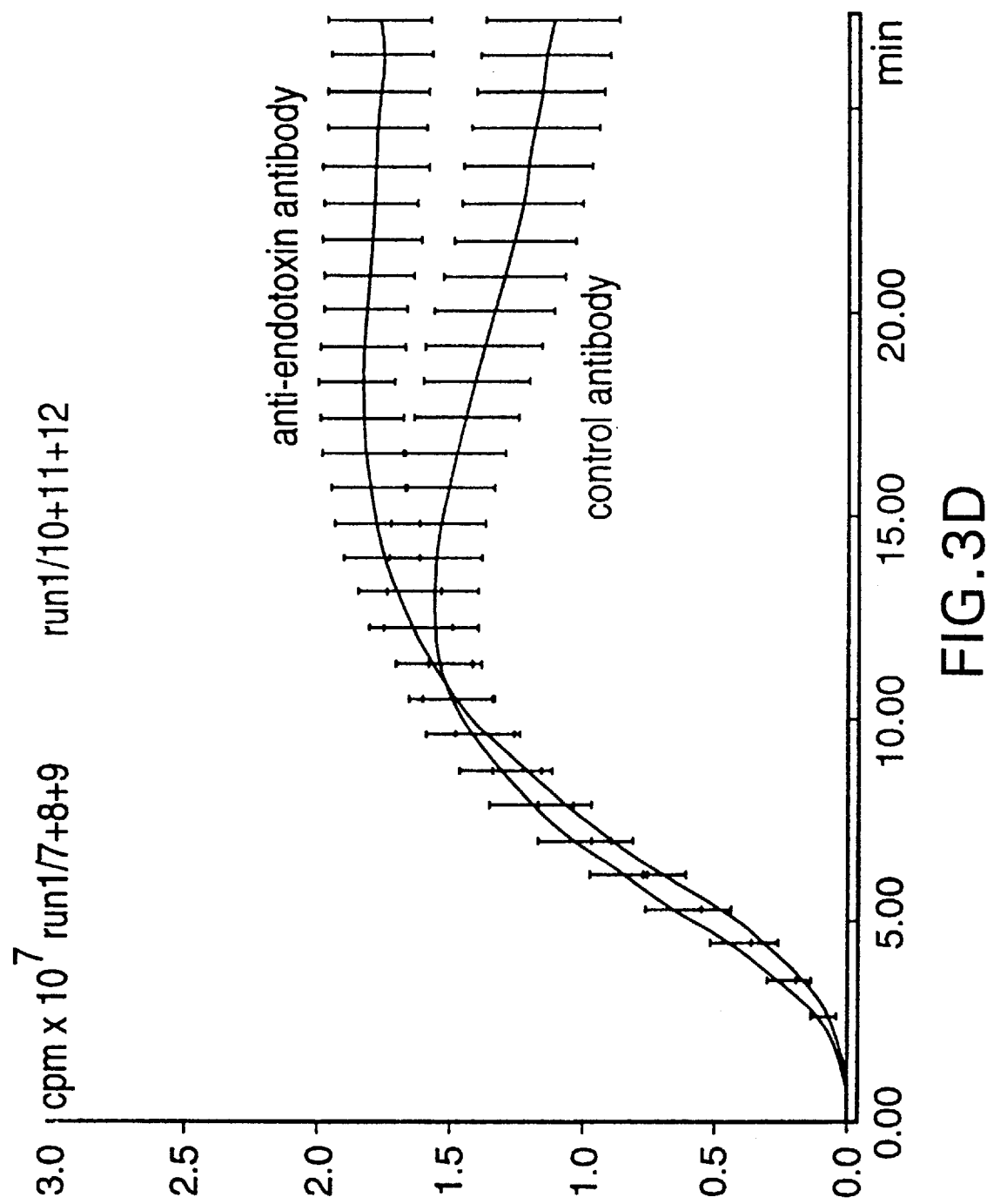
FIG. 3D uses blood from a patient with severe sepsis syndrome which contributed to his death 3 days after the sample was taken. This patient had no evidence of gram-negative endotoxemia or bacteremia.
Figure 3E:
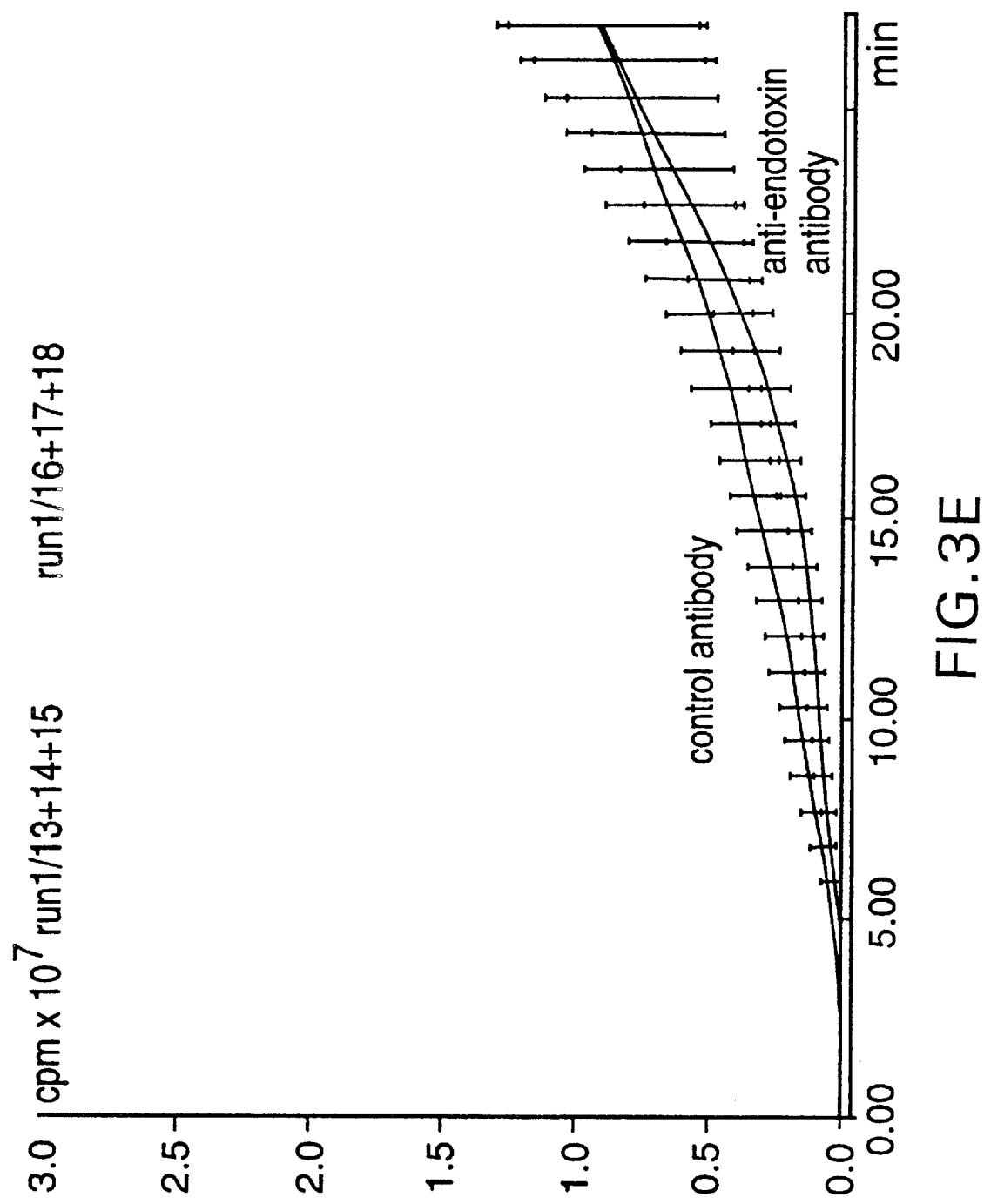
FIG. 3E uses blood from a patient being weaned from respiratory support and seriously cachectic, but with no clinical evidence of any septic foci.

Example VIII
Initial Correlation Analysis Between Chemiluminescent Assay of Endotoxin and a Standard Reference Method Employing the Limulus Amebocyte Lysate (LAL) Assay In this study, arterial blood samples were taken from patients with clinical symptoms of sepsis into sterile EDTA-containing vacutainer tubes and assayed for the presence of endotoxin by both the chemiluminescent whole blood assay and the reference limulus amebocyte lysate assay using assay kits purchased from BioWhittaker (Walkerville, Md., U.S.A.) or Seikagaku Kogyo Ltd. (Tokyo, Japan). Control samples were also obtained from non-septic patients and healthy ambulatory donors. FIG. 3A uses blood from a patient with severe sepsis syndrome who died 6 hours after the sample was taken. FIG. 3B uses blood from a healthy ambulatory volunteer. FIG. 3C uses blood from a patient with chronic sepsis. FIG. 3D uses blood from a patient with severe sepsis syndrome who died 3 days after the sample was taken but had no evidence of gram-negative infection. FIG. 3E uses blood from a patient with no clinical evidence of any septic foci but with severe cachexia. All blood transfer and reagent dispensing for both assays was accomplished using endotoxin-free pipettes and sterile practice. The chemiluminescence assay mixture was composed of 50 µl of undiluted anti-coagulated whole blood, 50 µl of antibody (concentration 0.2 mg IgM/ml) and 200 µl of luminol solution and 50 µl of complement opsonized zymosan. All reagents were added in the order listed and the first two solutions were pre-incubated at 37° C. for 5 minutes prior to the addition of luminol and zymosan, followed by the initiation of CL readings which were monitored for up to 60 minutes. All chemiluminescence assays were always run in conjunction with blood obtained from non-septic patients and ambulatory lab staff to verify the absence of false positive results. A positive control sample containing blood supplemented in vitro *E. coli* LPS at a concentration of 100 pg/ml was always assayed with each run of patient samples.

Parallel blood samples from patients and controls were centrifuged at 700× g for 15 minutes to remove cells and duplicate 50 µl aliquots of plasma were removed using endotoxin free pipettes and transferred into endotoxin-free glass test tubes for LAL assay. The plasma was treated with endotoxin free perchloric acid to remove inhibitory factors according to the procedure of Inada K., et al. *CRC Review on Gram-negative Endotoxin* 225 (1989) and subsequently assayed for endotoxin using the high sensitivity protocol as specified by Seikagaku Kogyo Inc (Toxicolor System Instruction Manual for Endotoxin Determination). The endotoxin levels were also confirmed using the LAL assay protocol for human plasma as specified by BioWhittaler.

In Example VIII, the response of the CL assay for endotoxin was compared to the standard Limulus Amebocyte Lysate (LAL) assay which is used by the pharmaceutical industry as a reference method for the detection of gram-negative endotoxin. In this initial study three patients were chosen who had clinical evidence of sepsis as determined by a certified Intensivist (a physician specializing in Intensive Care medicine) in the Surgical Intensive Care unit at The Toronto Hospital, and two patients who had no clinical evidence of sepsis (one of these samples was obtained from a healthy ambulatory volunteer and the other sample from and ICU patient who was being weaned from respiratory support). FIG. 3A displays the chemiluminescent response of blood taken from the radial artery of a patient with severe sepsis syndrome who had died 6 hours after the sample was taken. The cause of death was hypotensive shock which was refractory to inotropic support. It is clear from the CL response in the presence of anti-LPS antibodies that this patient had a high level of endotoxin which was confirmed by LAL assay to be on the order of greater than 700 pg/ml (see Table 8). Even with such high levels of antigen which would result in high levels of mediators and thereby white blood cell activation, the antigen/antibody formation still causes an increase in white blood cells oxidant production. FIG. 3B illustrates the CL profile of a healthy ambulatory volunteer and shows no differential response to anti-LPS antibody which was confirmed by LAL assay to indicate the absence of LPS in the blood. FIG. 3C displays the CL response of a patient with chronic sepsis which was confirmed by blood culture to be primarily due to a beta hemolytic gram positive streptococcus. The CL assay indicated that this patient also had a response consistent with a low level of gram-negative septicemia which was below the limits of detection when assayed by LAL. The limit of detection using the Seikagaku Kogyo Endospecy LAL assay was a whole blood concentration of 50 pg/ml LPS. In order to remove interfering substances this LAL assay requires a perchloric acid pre-treatment step which results in a tenfold dilution of the blood which is added to the assay mixture. This step poses a major limit on the analytical sensitivity of the assay. FIG. 3D displays the CL response of a patient who had severe sepsis syndrome which ultimately contributed to his death 3 days after the blood sample used for the analysis was taken. The CL analysis indicated no evidence of LPS in the blood which was confirmed by LAL assay. The microbiological reports on culture material for this patient suggested that he had gram positive sepsis. FIG. 3E represents the results of a CL assay for LPS conducted on blood obtained from a patient who was being weaned from respiratory support and was previously cachectic, but had no clinical evidence of any septic foci. The LAL assay confirmed the absence of endotoxin. These results suggest that the CL assay devised for the rapid detection of gram-negative endotoxin is capable of detecting LPS in patents with sepsis syndrome in whom LPS is detectable by standard LAL assay. In one patient (FIG. 3C), gram-negative endotoxin was detectable by CL assay but probably below the limits of detection based on the LAL assay. The sensitivity and rapidity of the CL assay confirms its great potential in the early detection and clinical management of patients with sepsis syndrome.

In a further comparison of the present invention's CL method and the LAL assay, patients were tested for the presence of LPS at different times and using varying antibody dilutions. The LPS values for the CL assay for each test closely matched the values for the LAL assay. These LPS results for the CL assay and LAL assay are shown in Table 9. These samples were assayed using both LAL assays (Seikagaku and BioWhittaker). The BioWhittaker assay was found to be sensitive below 50 pg/ml of LPS as compared to the Seikagaku assay protocol.

Example IX
Chemiluminescent Response of Whole Blood from a Septic Patient Using Three Concentrations of Antibody The patient had recurrent problems with a leaky duodenal ulcer. The patient experienced a temperature spike in the morning. The blood sample was taken approximately four hours before he was taken to the OR for abdominal cavity lavage.

A preferred approach for testing patient samples for endotoxin is based upon the following assay conditions: 20 microliters of the patient's blood (EDTA anti-coagulated) is mixed with 20 $\mu$l (microliter) of antibody (three different dilutions are used, 0.2, 0.002 and 0.002 mg/ml) in an endotoxin free assay cuvette. The mixture is incubated for 10 minutes at 37° C. and then 200 $\mu$l of luminol solution (40 $\mu$M) is added (pre-equilibrated to a temperature of 37° C.) followed by 50 $\mu$l of complement opsonized zymosan 2.5–3.0×10$^9$ particles/ml. Measurement of emitted light is then initiated in the chemiluminometer.

Figure 4:
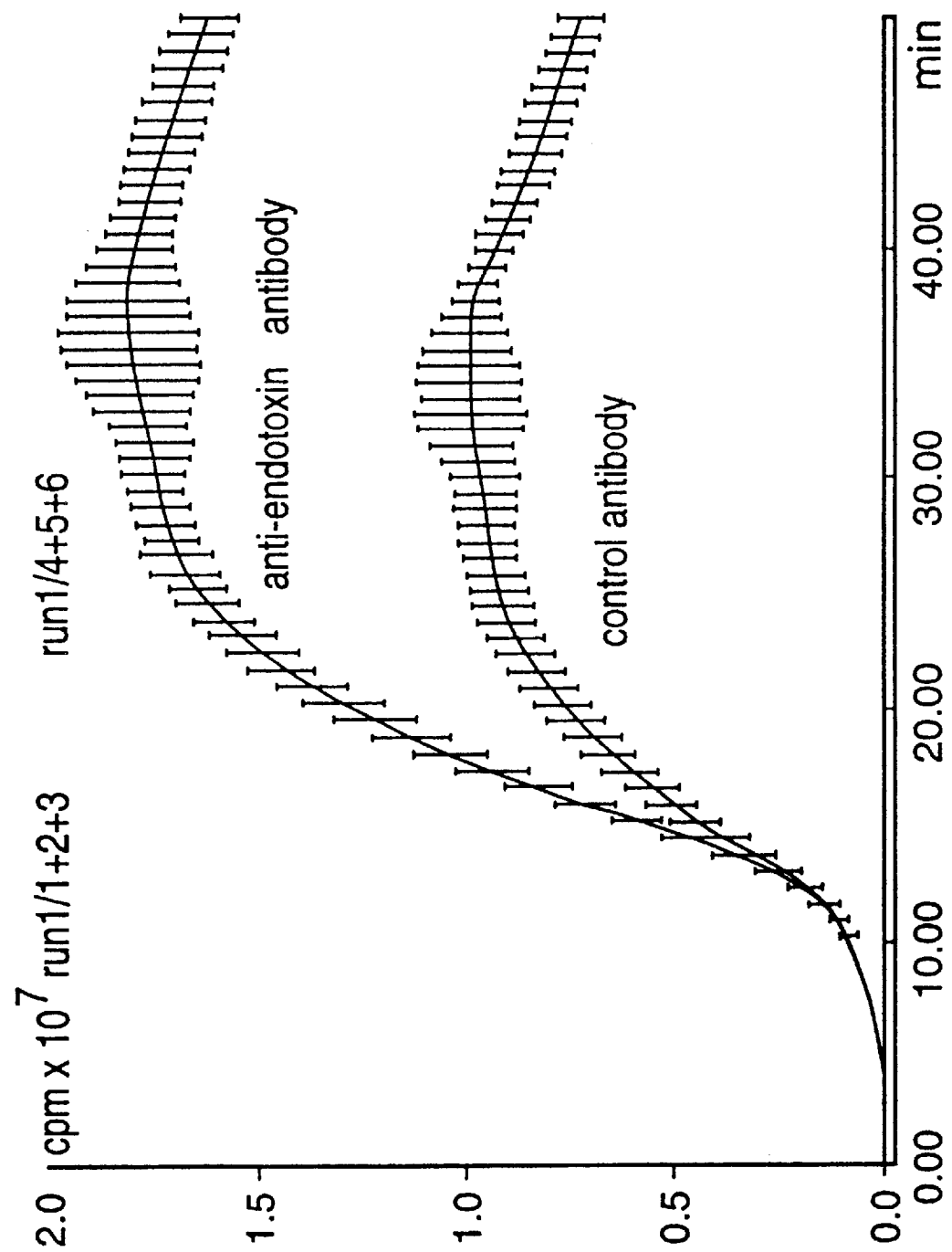
FIG. 4 is the chemiluminescent response using blood from a patient with a leaky duodenal ulcer.

As demonstrated in FIG. 4 (using the preferred patient assay format) a significant difference between control and anti-endotoxin antibodies can be achieved within 20 minutes. The assay is shown only for the antibody concentration of 0.2 mg/ml since the other antibody concentrations gave no differential response between control and anti-endotoxin antibody. The upper tracing in the Figure depicts the CL response of anti-endotoxin antibody containing blood, while the lower panel depicts the pattern achieved with a non-specific control antibody. The patient's sample was confirmed to contain 420 pg/ml of gram-negative endotoxin in LAL assay. The format of this assay was designed to minimize the amount of antibody necessary to evoke a significant chemiluminescence enhancement in the presence of gram-negative endotoxin. For this reason only patient sample and the antibody are incubated in the first phase of the reaction sequence in order to maximize effective antibody antigen complex formation. This preferred format has been adopted for patient studies.

FIG. 4 demonstrates clearly the difference in the chemiluminescence levels of the patient as compared to the control using an antibody concentration of 0.2 mg/ml.

Example X
Effects of a Maximum Stimulatory Concentration of C5a of Whole Blood Chemiluminescence in a Blood Sample Obtained from a Patient with Septic Shock and a High Blood Endotoxin Concentration (>700 pg/ml)

As indicated in Table 10, complement anaphylatoxin C5a at a dose which stimulates maximum opsonin receptor expression had no effect on the ratio of integrated light intensity observed in the presence of control antibody versus specific anti-LPS antibody. The concentration of anti-LPS IgM antibody and the irrelevant IgM antibody are 0.2 mg/ml and the concentration of C5a is 10 pg/sample. The patient chosen for this study had an endotoxin level >700 pg/ml by LAL assay using the plasma assay procedure protocol of BioWhittaker Inc. (Walkerville, Md.) or Seikagaku Kogyo (Tokyo, Japan). A blood sample from this patient was obtained for assay of endotoxin using control and anti-LPS antibody in the presence and absence of complement opsonized zymosan. As shown in Table 10, the addition of C5a at a dose which recruits maximum opsonin receptor expression had no effect on the ratio of integrated light intensity observed with control versus anti-LPS antibody. The C5a was added to the blood samples immediately after the 5 minutes incubation of blood with antibody and the samples were then incubated an additional 5 minutes at 37° C. prior to the additional of luminol solution. In the absence of opsonized zymosan, C5a increased the whole blood chemiluminescence of both control and anti-LPS assay samples but had no effect on the ratio of control versus anti-LPS assay samples in terms of integrated light intensity. Similarly, in the presence of complement opsonized zymosan, C5a had no effect on the same ratio. In addition C5a had a minimal effect on the opsonized zymosan-containing assay tubes, causing only a slight increase in chemiluminescent light release. This is indicative of the fact that the patients blood already had virtually maximal opsonin receptor expression in the absence of C5a. The addition of C5a only increased the chemiluminescent response by about 10% in assay samples containing opsonized zymosan. These results clearly demonstrate the formation of antigen-antibody complexes in the form of LPS—anti-LPS antibody complexes in patient samples containing endogenous LPS, and the subsequent effect of these complexes on white cell chemiluminescence is independent of opsonin receptor expression and proceeds via an activation pathway which does not depend upon differential opsonin receptor expression.

Figure 5:
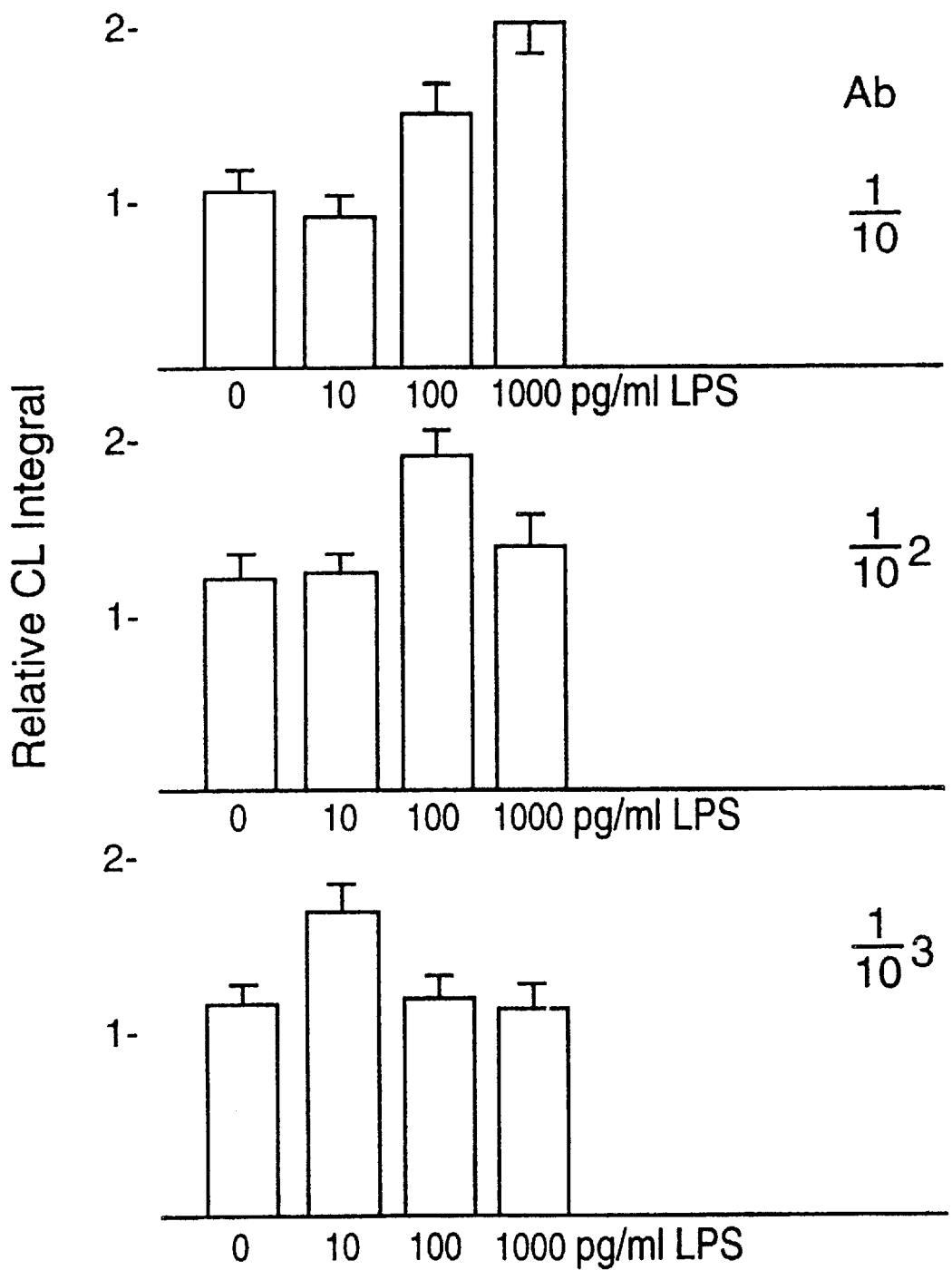
FIG. 5 is the whole blood chemiluminescence response using varying concentrations of endotoxin with varying concentrations of antibody against the endotoxin.

Example XI
Illustration of Optimal Antigen-Antibody Complementarily Using a Clinically Significant Range of LPS Concentrations These experiments summarized in FIG. 5 demonstrate the dependence of the whole blood chemiluminescence response on antigen (LPS) and antibody concentration (Xomen-E5 0.2, 0.02 and 0.002 mg/ml). The maximal chemiluminescence generated at an LPS concentration of 1000 pg/ml is achieved at an antibody concentration of 0.2 mg/ml (top panel) and for an LPS concentration of 10 pg/ml at an antibody concentration 0.002 mg/ml (bottom panel). As indicated in FIG. 5, a baseline sample is included containing the specific antibody but no LPS. A baseline sample is included at each concentration of antibody used. This study was conducted using the standard assay format. Twenty $\mu$l of EDTA anti-coagulated whole blood was mixed with 20 $\mu$l of the respective antibody concentration and incubated at 37° C. for 5 minutes followed by the addition of 200 $\mu$l of luminol solution and then 50 $\mu$l of complement-opsonized zymosan. The integrated light intensity was collected for 30 minutes and is expressed on a relative scale in FIG. 5. This experiment illustrates the dependence of the chemiluminescence signal on the optimal antigen/antibody complementarity.

Example XII
Effects of Heat Labile Factors in Plasma on the Chemiluminescence Response to Antigen—Antibody Complexes In this experimental series standard assay protocol was adopted using a monoclonal anti-LPS IgM antibody (Xomen E5) concentration of 0.2 mg/ml and an endotoxin concentration of 1000 pg/ml. The effect of heat treatment of the plasma prior to the formation of antigen/antibody complexes was examined. EDTA-anticoagulated whole blood was centrifuged at 1500× g for 15 minutes to separate plasma from cells. The plasma fraction was then carefully removed and incubated for 30 minutes at 25° C. or at 56° C. and then added back to the cell fraction. Fifty $\mu$l of whole blood (plasma fraction treated at room temperature or at 56° C.) was then mixed with an equal volume of antibody solution and incubated at 37° C. for 5 minutes with subsequent addition of luminol solution (200 microliters) and complement-opsonized zymosan (50 $\mu$l). The resulting chemiluminescence signal was then measured for 60 minutes and the peak CL count was recorded. An identical assay protocol using whole blood without centrifugation and heating was included for comparison. As shown in Table 11, the prior heating of the plasma component of whole blood abolished the increased chemiluminescent response to antigen/antibody complexes. This experiment suggests that a heat labile component of plasma, likely a protein(s) of the complement pathway, is necessary for activation of increased white cell chemiluminescence following the formation of antigen/antibody complexes.

Example XIII
Lack of Chemiluminescent Response with *E. coli* in Whole Blood Unless Antibody is Added

*E. coli* was isolated from a patient with gram negative sepsis. An isolate of the bacterium was cultured on agar and suspended in liquid medium at a density of approximately 1 million bacteria per ml. Aliquots of this mixture were added to whole blood and tested for chemiluminescence response in the presence of murine ascites fluid containing an IgM directed against LPS epitopes (Table 12). The source of the monoclonal IgM antibody was QED Laboratories in La Jolla, Calif., U.S.A. Experiments showed the ability to detect bacteria at concentrations of $10^4$ bacteria per ml of whole blood. In these experiments the chemiluminescent response was triggered with opsonized zymosan. Samples containing bacteria and antibody together showed an augmented response compared to blood neutrophil chemiluminescence in the absence of antibody. *E. coli* in a concentration of $10^5$/ml whole blood had no detectable effect on whole blood chemiluminescence after pre-incubation of whole blood for 30 or 60 minutes with the bacteria.

Example XIV
Chemiluminescence Response Decreases with IgG for Hepatitis A

A murine monoclonal antibody to human Hepatitis A virus of the IgG class was tested for its ability to detect the virus in whole blood at antibody dilutions of 1/50, 1/200 and 1/1,000 against antigen dilutions of 1/50 and 1/500 of the stock viral antigen solution which contained approximately 100 μg/ml of viral protein. The Hepatitis A virus was killed and was at a protein concentration of 100 μg/ml and the anti-Hepatitis A antibody was a murine IgG at a protein concentration of 1 mg//ml. The Hepatitis A virus and antibody were available from ADI of Mississauga, Ontario, Canada. The test procedure was that of Example IX. In these experiments, a converse suppressive effect of viral antigen-antibody complexes on whole blood chemiluminescence was observed. This effect may be due to the binding of antigen/antibody complexes directly to the neutrophil Fc receptors, followed by complement mediated cytolysis of neutrophils by the membrane attack complex. Such a response would diminish the chemiluminescence response in samples containing a combination of antigen and antibody, relative to the antibody alone.

Example XV
Quantitative use of the Whole Blood Chemiluminescence Assay in the Detection of Gram Negative Endotoxin (LPS).

Figure 6:
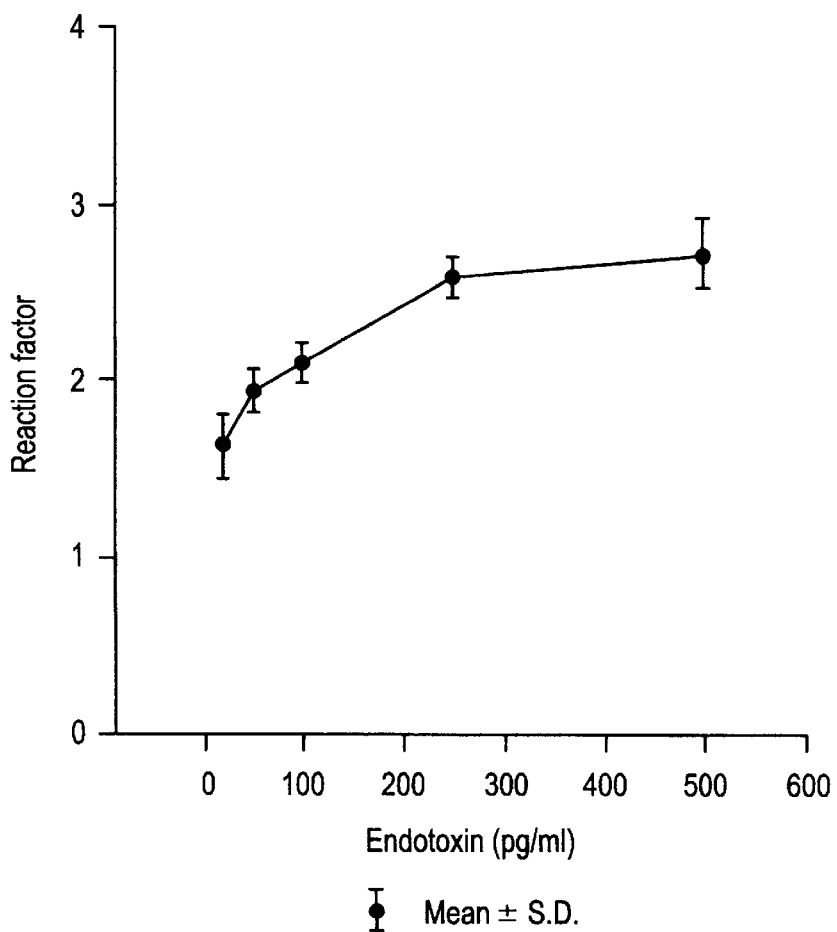
FIG. 6 shows results from the whole blood chemiluminescence response using varying concentrations of endotoxin with a fixed concentration of antibody against the endotoxin. Results are shown in linear form.
Figure 7:
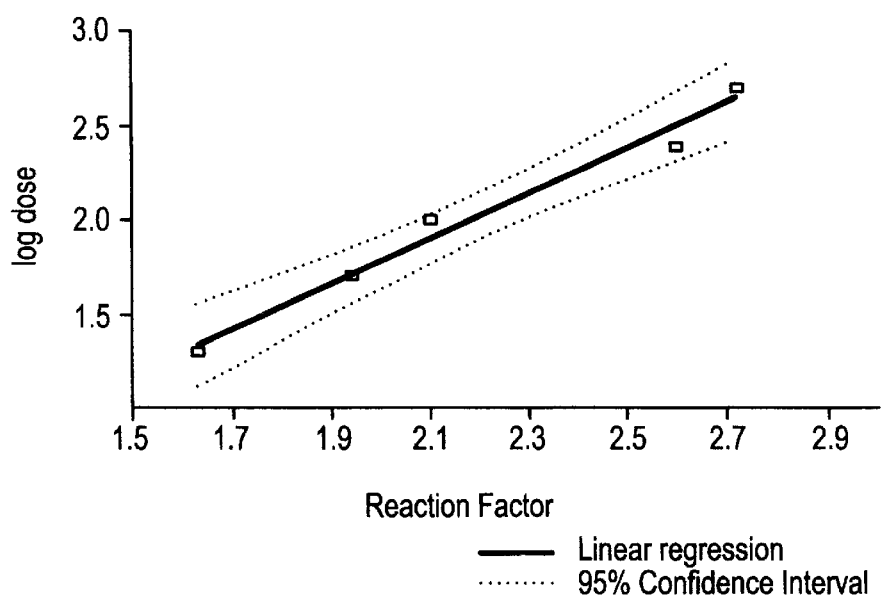
FIG. 7 shows results from the whole blood chemiluminescence response using varying concentrations of endotoxin with a fixed concentration of antibody against the endotoxin. Results are shown in logarithmic form.

The ability of the Xomen-E5 antibody to yield a quantitative assay of endotoxin in whole blood at a fixed concentration of antibody was investigated. In this assay strategy, an assay mixture was employed containing 50 μl of antibody (either Xomen—E5 or non-specific control both at a concentration of 0.05 mg/ml) which was mixed with 16 μl of whole blood and incubated at room temperature for 5 minutes. To this mixture was added a luminol-containing buffer solution (600 μl) which was warmed to 37° C. and 50 μl of human complement opsonized zymosan. All samples were assayed in triplicate with control and Xomen-E5 antibody. To three separate blood samples obtained from three endotoxin free donors (including on ICU patient and two lab volunteers) varying concentrations of *E. coli* endotoxin were added yielding final endotoxin concentrations of 20, 50, 100, 250 and 500 pg/ml of whole blood. These blood samples were assayed utilizing the protocol above with control and anti-endotoxin antibodies. Total light integrals were obtained for the mean reaction curves for the anti-endotoxin and control antibody containing samples at 20 minutes of total reaction time. For each endotoxin concentration the light integral for the control antibody-containing samples was subtracted from the light integral of the E5 antibody containing samples and divided by the light integral of the control antibody-containing samples to normalize for differences in white cell count and white cell reactivity. This calculation yielded a "reaction factor" which was then plotted against the endotoxin concentration. The relationship between the response factor and antibody concentration is displayed in both linear and semi-logarithmic form. It is therefore possible to use the response factor calculated from patient samples to interpolate the calibration curve and hence estimate the endotoxin concentration contained within an unknown sample. Results are shown in FIGS. 6 and 7.

It is commonly believed that during bacterial infection phagocytes are activated by endotoxin and also cytokines. Experiments with antibodies against tumor necrosis factor (TNF) have detected this cytokine using the same principle employed in the endotoxin assay. This confirms the generic nature of the reaction sequence of this invention. This invention provides a diagnostic screening technology for detecting sepsis due to a variety of agents. The invention may be used particularly with monoclonal antibodies against the following:

1) Bacteria Gram-negative, for example with antibodies directed against Lipid A, O-saccharides or O-antigens, Gram positive, for example with antibodies directed against lipoteichoic acid, 2) Viruses and viral particles.

3) Fungae, in particular, Candida.

In addition, monoclonal antibodies against inflammatory mediators, such as, TNF, interleukins 2, 6, 8, Interferon-γ and transforming growth factor β, will indicate the presence and degree of sepsis in the patient.

As an added diagnostic feature of this invention, the invention can be used to titrate a patient's therapeutic antibody titre and to evaluate the effectiveness of antibody therapy in reducing endotoxin levels. By conducting a simultaneous panel of tests using antibodies against TNF, IL-1, IL-6 and other markers of sepsis it is possible to establish a "sepsis panel" to indicate the degree and magnitude of sepsis progression. A septic panel would use a combination of monoclonal antibodies against bacteria, virus or fungae and inflammatory mediators. Each tube could contain a different monoclonal antibody to test the patient sample for a variety of septic indicators. One panel kit could include antibodies to the most common types of bacterial toxins, for example, antibody against gram-negative bacterial endotoxin and antibody against gram-positive bacteria lipoteichoic acid. Another panel kit could have antibodies against the viral or fungal antigens which are associated with sepsis. Another panel kit could have antibodies against the inflammatory mediators to determine the patient's immune activation in response to sepsis.

Thus this invention allows for the diagnosis and staging of patients septic condition and also the evaluation of the efficacy of therapeutic treatments. A sepsis panel provides information on a range of sepsis indicators to better indicate the degree of progression of sepsis. Identifying those patients at risk of sepsis is important for initiating effective therapeutic treatment. The invention is easily performed, requiring only three reagents and a luminometer. This test can be used to serially monitor a patient, for example by conduction the test three or four times a day or more as clinical conditions or therapeutic interventions warrant.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

TABLE 1

TURBIDOMETRIC ASSAY OF LPS-AntiLPS ANTIGEN-ANTIBODY COMPLEX FORMATION ($\lambda$ = 340 nm. Absorbance at 5 min. time point × $10^{-2}$)

| Antibody concentration | LPS concentration (µg/ml) | | | |
|---|---|---|---|---|
| (µg/ml) | 100 | 10 | 1 | 0.1 |
| 200 | 6.31 | 8.48 | 7.96 | 8.1 |
| 20 | 2.8 | 2.6 | 2.58 | 2.53 |
| 2 | 0.33 | 0.14 | 0.1 | 0.11 |
| 0.2 | 0.08 | 0.01 | 0.02 | 0 |

TABLE 2

EFFECT OF VARYING AntiLPS ANTIBODY CONCENTRATIONS ON CHEMILUMINESCENT RESPONSE OF WHOLE BLOOD IN PRESENCE AND ABSENCE OF LPS Values of chemiluminescence are given as 30 min. integral × $10^7$

| Antibody concentration (µg/ml) | No LPS | LPS (1 ng/ml) |
|---|---|---|
| 100 | 3.07 ± 0.20 | 2.03 ± 0.22 |
| 10 | 3.09 ± 0.13 | 2.85 ± 0.06 |
| 1 | 4.04 ± 0.02 | 4.22 ± 0.07 |
| 0.1 | 4.64 ± 0.14 | 4.65 ± 0.15 |
| 0.01 | 4.90 ± 0.19 | 5.71 ± 0.36 |

TABLE 3

EFFECT OF LPS ON WHOLE BLOOD CHEMILUMINESCENT IN PRESENCE AND ABSENCE OF AntiLPS ANTIBODY Values of chemiluminescence are given as 30 min. integral × $10^7$

| NO LPS | LPS (1 ng/ml) |
|---|---|
| Panel A. No Antibody | |
| 1.26 ± 0.05 | 1.16 ± 0.02 |
| Panel B. Antibody (1.3 µg/ml) | |
| 1.36 ± 0.06 | 1.91 ± 0.13 |

TABLE 4

EFFECT OF LPS ON WHOLE BLOOD CHEMILUMINESCENCE IN PRESENCE AND ABSENCE OF AntiLPS ANTIBODY Values of chemiluminescence are given as 5 min. integral × $10^6$

| Antibody concentration | LPS concentration (pg/ml) | | |
|---|---|---|---|
| (µg/ml) | 0 | 100 | 1000 |
| 0.2000 | 1.47 ± 0.01 | 3.11 ± 0.03 | 1.05 ± 0.06 |
| 0.067 | 1.80 ± 0.13 | 2.56 ± 0.13 | 1.93 ± 0.10 |
| 0.022 | 2.35 ± 0.20 | 2.27 ± 0.05 | 3.51 ± 0.32 |
| 0.007 | 3.25 ± 0.22 | 2.02 ± 0.09 | 5.58 ± 0.46 |
| 0.002 | 3.34 ± 0.13 | 1.95 ± 0.11 | 3.07 ± 0.21 |

TABLE 5

CHEMILUMINESCENT RESPONSE OF WHOLE BLOOD, CONTAINING IN VITRO ADDED LPS WITH ADDITION of AntiLPS ANTIBODY BUT NO ZYMOSAN Values of chemiluminescence are given as 20 min. integral × $10^3$ PANEL A. CL response without LPS

| Control antibody (0.2 mg/ml) | AntiLPS antibody (0.2 mg/ml) |
|---|---|
| 9.76 ± 0.90 | 36.4 ± 1.52 |

PANEL B. CL response with added LPS (1 ng/ml)

| Control antibody (0.2 mg/ml) | AntiLPS antibody (0.2 mg/ml) |
|---|---|
| 9.22 ± 0.25 | 68.5 ± 2.50 |

PANEL C. Effect of different LPS concentration on whole blood chemiluminescence with AntiLPS antibody (0.2 mg/ml)

| LPS concentration (pg/ml) | Chemiluminescence |
|---|---|
| 0 | 48.8 ± 1.40 |
| 10 | 61.7 ± 3.20 |
| 50 | 62.9 ± 2.70 |
| 100 | 100 ± 2.20 |

TABLE 6

CHEMILUMINESCENT RESPONSE OF WHOLE BLOOD, TO IN VITRO ADDED LPS AT VARYING CONCENTRATION OF AntiLPS ANTIBODY Values of chemiluminescence are given as 60 min. integral × $10^7$

| Antibody concentration (µg/ml) | NO LPS | LPS (10 pg/ml) |
|---|---|---|
| PANEL A. Preincubation of blood with LPS and AntiLPS antibody for 5 min. | | |
| 0.002 | 4.39 ± 0.71 | 4.66 ± 0.16 |
| 0.02 | 3.09 ± 0.64 | 3.88 ± 0.69 |
| 0.2 | 3.86 ± 0.45 | 5.40 ± 0.37 |
| 2 | 4.19 ± 0.62 | 4.55 ± 0.59 |
| 20 | 3.84 ± 0.54 | 3.71 ± 0.41 |
| 200 | 3.98 ± 0.30 | 7.68 ± 0.56 |
| PANEL B. Preincubation of blood with LPS and AntiLPS antibody for 1 hr. | | |
| 0.002 | 4.81 ± 0.40 | 5.20 ± 0.30 |
| 0.02 | 5.48 ± 0.21 | 5.07 ± 0.46 |
| 0.2 | 5.29 ± 0.46 | 5.02 ± 0.58 |
| 2 | 5.15 ± 0.14 | 5.06 ± 0.07 |
| 20 | 5.35 ± 0.42 | 5.26 ± 0.61 |
| 200 | 6.82 ± 1.46 | 3.45 ± 0.18 |

TABLE 7

CHEMILUMINESCENT RESPONSE OF WHOLE BLOOD TO IN VITRO ADDED LPS AND AntiLPS (0.2 mg/ml)
Values of chemiluminescence are given as slope (c.p.m./min. × $10^6$) at 10 min.

| Control antibody | AntiLPS antibody |
|---|---|
| PANEL A. No LPS added | |
| 0.113 | 0.133 |
| PANEL B. LPS (5 pg/ml) | |
| 0.114 | 0.159 |
| PANEL C. LPS (50 pg/ml) | |
| 0.116 | 0.219 |
| PANEL D. LPS (500 pg/ml) | |
| 0.113 | 0.226 |

TABLE 8

LAL ASSAY FOR LPS:
RESULTS OF ANALYSIS ON ENDOTOXIN STANDARDS IN WHOLE BLOOD AND PATIENT SAMPLES

| Origin of Blood | Optical Density Mean Value | LPS Conc. pg/ml of Original Sample |
|---|---|---|
| blank | 0.003 | 0 |
| standard 1 | 0.166 | 1000 |
| standard 2 | 0.087 | 500 |
| standard 3 | 0.020 | 100 |
| panel A | 0.125 | 753 |
| panel B | 0.005 | 0 |
| panel C | 0.004 | 0 |
| panel D | 0.007 | 0 |
| panel E | 0.007 | 0 |

TABLE 9

COMPARISON OF LPS RESULTS BETWEEN CL METHOD AND LAL ASSAY IN PATIENTS WITH CLINICAL SEPSIS

| Patient | CL Assay Result pg/ml LPS | Ab Dilution | LAL Assay pg/ml |
|---|---|---|---|
| M. O. | >100 | 1:10 | 130 |
| M. O. | 20–50 | 1:100 | 40 |
| M. O. | >200 | 1:10 | 400 |
| J. S. | 20–50 | 1:100 | 50 |
| J. S. | Neg. | | Neg. |
| J. S. | >100 | 1:10 | 90 |
| M. P. | >100 | 1:10 | 120 |
| P. S. | Neg. | | Neg. |
| P. S. | Neg. | | Neg. |
| P. S. | Neg. | | Neg. |
| J. V. | >200 | 1:10 | >700 |
| J. V. | >200 | 1:10 | 750 |
| M. H. | 20–50 | 1:100 | 60 |

TABLE 10

EFFECTS OF A MAXIMUM STIMULATORY CONCENTRATION OF C5a ON WHOLE BLOOD CHEMILUMINESCENCE IN A BLOOD SAMPLE CONTAINING A HIGH ENDOTOXIN CONCENTRATION OBTAINED FROM A SEPTIC PATIENT (LPS > 700 pg/ml)

| Assay Components | Light Integral (30 min) | % CV | Ratio of Light Integral Control vs anti-LPS Ab |
|---|---|---|---|
| Patient Blood + Control Ab | $1.2 \times 10^5$ | 16 | |
| Patient Blood + anti-LPS Ab | $2.3 \times 10^5$ | 15 | 0.52 |
| Patient Blood + Control Ab + C5a | $1.77 \times 10^6$ | 13 | |
| Patient Blood + anti-LPS Ab + C5a | $3.5 \times 10^6$ | 15 | 0.51 |
| Patient Blood + Control Ab + opZym | $5.45 \times 10^8$ | 7 | |
| Patient Blood + anti-LPS Ab + opZym | $14.9 \times 10^8$ | 4.9 | 0.37 |
| Patient Blood + Control Ab + opZym + C5a | $6.0 \times 10^8$ | 7.6 | |
| Patient Blood + anti-LPS Ab + opzym + C5a | $15.7 \times 10^8$ | 5.4 | 0.38 | opZym = human complement opsonized zymosan

TABLE 11

EFFECTS OF HEAT TREATMENT OF PLASMA ON THE CHEMILUMINESCENCE SIGNAL MAXIMUM IN THE PRESENCE OF ANTIGEN - ANTIBODY COMPLEXES

| Assay Components | Mean CL Signal Maximum (CPM) | % CV |
|---|---|---|
| Blood + anti-LPS IgM | $2.4 \times 10^6$ | 3 |
| Blood + anti-LPS IgM + Endotoxin | $3.3 \times 10^{6*}$ | 1.8 |
| Blood + anti-LPS IgM (Plasma stored at 25° C.) | $2.1 \times 10^6$ | 2.5 |
| Blood + anti-LPS IgM (Plasma heated at 56° C.) + Endotoxin | $2.1 \times 10^6$ | 2.3 |

* = P < 0.01 vs Blood + anti-LPS IgM, paired t test, n = 6.

TABLE 12

E. COLI WHOLE BLOOD CHEMILUMINESCENCE EXPERIMENTS

| Mass of Ab per reaction in mg | E. Coli conc. Bacteria/ml blood | Light Integral | CV % | Peak CPM |
|---|---|---|---|---|
| 0.014 | $10^5$ | $1.22 \times 10^8$ | 8.7 | $3.1 \times 10^6$ |
| 0.014 | None | $0.996 \times 10^8$ | 15 | $2.78 \times 10^6$ |
| 0.0028 | $5 \times 10^4$ | $1.30 \times 10^8$ | 2.5 | $3.55 \times 10^6$ |
| 0.0028 | None | $0.95 \times 10^8$ | 16 | $2.69 \times 10^6$ |
| 0.0028 | $10^5$ | $1.4 \times 10^8$ | 6.8 | $3.7 \times 10^6$ |
| 0.0028 | None | $0.94 \times 10^8$ | 16 | $2.65 \times 10^6$ |

TABLE 13

HEPATITIS A VIRUS CHEMILUMINESCENCE EXPERIMENTS

| Antibody Dilution | Antigen Dilution | Light Integral | CV % | Peak CPM | CV % |
|---|---|---|---|---|---|
| 1/50 | 1/50 | $1.28 \times 10^8$* | 1.2 | $3.33 \times 10^6$ | 1.7 |
| 1/50 | No Ag | $1.46 \times 10^8$* | 3.2 | $3.60 \times 10^6$ | 3.2 |
| 1/200 | 1/50 | $1.31 \times 10^8$* | 13 | $3.98 \times 10^6$ | 14 |
| 1/200 | No Ag | $2.24 \times 10^8$* | 8 | $6.63 \times 10^6$ | 8 |
| 1/1000 | 1/50 | $1.33 \times 10^8$* | 15 | $3.87 \times 10^6$ | 16 |
| 1/1000 | No Ag | $2.81 \times 10^8$* | 13 | $8.52 \times 10^6$ | 14 |
| 1/50 | 1/500 | $1.62 \times 10^8$* | 1.3 | $5.0 \times 10^6$ | 4 |
| 1/50 | No Ag | $2.09 \times 10^8$* | 7 | $6.4 \times 10^6$ | 5.3 |
| 1/200 | 1/500 | $1.31 \times 10^8$* | 4 | $3.9 \times 10^6$ | 4 |
| 1/200 | No Ag | $1.5 \times 10^8$* | 11 | $4.6 \times 10^6$ | 12 |
| 1/1000 | 1/500 | $2.98 \times 10^8$* | 2 | $8.5 \times 10^6$ | 2.8 |
| 1/1000 | No Ag | $4.31 \times 10^8$* | 5 | $12.35 \times 10^6$ | 4.7 |

*All differences were statistically significant by paired "t" test at $p < 0.05$ Although preferred embodiments of the invention are described herein in detail, it will be understood by those skilled in the art that variations may be made thereto without departing from the spirit of the invention or the scope of the appended claims.

What is claimed is:

1. A method for determining the presence or extent of an infection in a human or animal patient by determining the amount of a preselected antigen indicative of said infection in a sample of said patient's blood, said sample comprising plasma and white blood cells, said method sequentially comprising:
   i) providing first and second aliquots of equal volume of said sample;
   ii) reacting the first aliquot of said sample with an amount of test antibody sufficient to form an antigen/antibody complex with said antigen, wherein said test antibody specifically binds to said antigen, to provide a test sample;
   iii) reacting the second aliquot of said sample with an equal amount of a control antibody wherein said control antibody (a) does not specifically bind said antigen and (b) is of the same class and species of origin as the test antibody, to provide a control sample;
   iv) incubating the test and control samples for a time sufficient for the antigen/antibody complex to react with the white blood cells and the complement proteins in the plasma to produce oxidants;
   v) contacting a chemiluminescent compound which reacts with said oxidants to generate luminscent light with either the test and control samples of steps ii) and iii) or with the test and control samples of step iv);
   vi) measuring light emission over a predetermined time period; and
   vii) correlating differences in light emission between the test and control samples to the presence or amount of said antigen in said sample and thereby to the presence or extent of the infection in the patient.

2. The method of claim 1 wherein said sample is whole blood.

3. The method of claim 1 wherein said white blood cells are selected from the group consisting of neutrophils, lymphocytes, monocytes and combinations thereof.

4. The method of claim 1 wherein sufficient zymosan is contacted with said test and control samples before step vi) to stimulate said production of oxidants.

5. The method of claim 1 wherein sufficient opsonized zymosan is contacted with said test and control samples before step vi) to stimulate said production of oxidants.

6. The method of claim 1 wherein sufficient opsonized latex beads are contacted with said test and control samples before step vi) to stimulate said production of oxidants.

7. The method claim 1 wherein said chemiluminescent compound is selected from the group consisting of luminol, lucigenin and pholasin.

8. The method of claim 7 wherein the chemiluminescent compound is luminol.

9. The method of claim 8 wherein sufficient zymosan is contacted with said test and control samples before step vi) to stimulate said production of oxidants.

10. The method of claim 8 wherein sufficient opsonized zymosan is contacted with said test and control samples before step vi) to stimulate said production of oxidants.

11. The method of claim 1, wherein the test sample and control sample in step i) are incubated with three dilutions of said test and control antibodies, said dilutions being 1:10, 1:100 and 1:1000, and wherein said correlating step further correlates said differences in light emission between said test samples and said control samples to the quantity of said antigen with the dilution which provides the greatest difference in light emissions.

12. The method of claim 11 wherein said test and control antibodies are IgM or IgG class monoclonal antibodies.

13. The method of claim 1 wherein the antigen is present on, released by or secreted by gram-negative bacteria, gram-positive bacteria, virus or fungus.

14. The method of claim 13, wherein the antigen is a Hepatitis A virus antigen.

15. The method of claim 13 wherein the antigen is gram-negative bacterial endotoxin lipid A.

16. The method of claim 15 wherein sufficient opsonized latex beads are contacted with said test and control samples before steps vi) to stimulate said production of oxidants.

17. A diagnostic kit for use in determining the extent of an infection in a human of animal patient by detecting the amount of a preselected antigen indicative of said infection in a sample of blood from said patient, said sample comprising plasma and white blood cells, said kit comprising:
   i) a first container of test antibody which specifically binds to said antigen,
   ii) a second container of chemiluminescent compound which reacts with oxidants produced by said white blood cells to generate luminescent light, and
   iii) a third container of control antibody which does not specifically bind said antigen and which is of the same class and species of origin as the test antibody.

18. The diagnostic kit of claim 17 wherein said antibodies are of the IgM class.

19. The diagnostic kit of claim 18 wherein said IgM test antibody specifically binds to a gram-negative bacterial endotoxin Lipid A.

20. The diagnostic kit of claim 17 wherein said antibodies are of the IgG class.

21. The diagnostic kit of claim 20 wherein said IgG test antibody specifically binds to Hepatitis A virus.

22. The diagnostic kit of claim 17 wherein said chemiluminescent compound is selected from the group consisting of luminol, lucigenin and pholasin.

23. The diagnostic kit of claim 17 further comprising a fourth container of zymosan or opsonized zymosan.

24. A method for determining the presence or extent of sepsis in a human or animal patient by determining the amount of a preselected sepsis marker in a sample of said patient's blood, said sample comprising plasma and white blood cells, said method sequentially comprising:
   i) providing first and second aliquots of equal volume of said sample;

ii) reacting the first aliquot of said sample with an amount of test antibody sufficient to form an antigen/antibody complex with said marker, wherein said test antibody specifically binds to said marker, to provide a test sample;

iii) reacting the second aliquot of said sample with an equal amount of a control antibody wherein said control antibody (a) does not specifically bind said marker and (b) is of the same isotype as the test antibody, to provide a control sample;

iv) incubating the test and control samples for a time sufficient for the antigen/antibody complex to react with the white blood cells and the complement proteins in the plasma to produce oxidants;

v) contacting a chemiluminescent compound which reacts with said oxidants to generate luminescen light with either the test and control samples of steps ii) and iii) or with the test and control samples of step iv);

vi) measuring light emission over a predetermined period; and vii) correlating differences in light emission between the test and control samples to the presence or amount of said marker in said sample and thereby to the presence or extent of the sepsis in the patient.

25. A method of claim 24 wherein said sample is whole blood.

26. The method of claim 24 wherein said white blood cells are selected from the group consisting of neutrophils, lymphocytes, monocytes and combinations thereof.

27. The method of claim 24 wherein the test sample and control sample in step i) are incubated with three dilutions of said test and control antibodies, said dilutions being 1:10, 1:100 and 1:1000, and wherein said correlating step further correlates said differences in light emission between said test samples and said control samples to the extent of said sepsis with the dilution which provides the greatest difference in light emissions.

28. The method of claim 24 wherein said test and control antibodies are IgM or IgG class monoclonal antibodies.

29. The method of claim 24 wherein the sepsis marker in an inflammatory mediator.

30. The method of claim 29 wherein the inflammatory mediator is selected from the group consisting of tumor necrosis factor, interleukin-1, interleukin-6, interleukin-8, interferon and transforming growth factor $\beta$.

31. The method of claim 30 wherein in the sample is whole blood.

32. A diagnostic kit for use in determining the presence or extent of sepsis in a human or animal patient by detecting the amount of a preselected sepsis marker in a sample of blood from said patient, said sample comprising plasma and white blood cells, said kit comprising:

i) a first container of test antibody which specifically binds to said marker, ii) a second container of chemiluminescent compound which reacts with oxidants produced by said white blood cells to generate chemiluminescent light, and ii) a third container of control antibody which does not specifically bind to said marker and which is of the same class and species of origin as the test antibody.

33. The diagnostic kit of claim 32 wherein said marker is an inflammatory mediator.

34. The diagnostic kit of claim 33 wherein the inflammatory mediator is selected from the group consisting of tumor necrosis factor, interleukin-1, interleukin-6, interleukin-8, interferon and transforming growth factor $\beta$.

35. The diagnostic kit of claim 32 wherein said antibodies are of the IgM class.

36. The diagnostic kit of claim 32 wherein said antibodies are of the IgG class.

37. The diagnostic kit of claim 32 wherein said chemiluminescent compound is selected from the group consisting of luminol, lucigenin and pholasin.

38. The diagnostic kit of claim 32 further comprising a fourth container of zymosan or opsonized zymosan.

* * * * *

UNITED STATES PATENT AND TRADEMARK OFFICE
CERTIFICATE OF CORRECTION

PATENT NO. : 5,804,370
DATED : September 8, 1998
INVENTOR(S) : Alexander D. Romaschin and Paul M. Walker It is certified that error appears in the above-indentified patent and that said Letters Patent is hereby corrected as shown below:

On the title page, item [73]:

Please change the Assignee from "Critichem Medical Products Limited" to read

--Sepsis, Inc.--

Signed and Sealed this

Tenth Day of August, 1999

*Attest:*

Q. TODD DICKINSON

*Attesting Officer*     *Acting Commissioner of Patents and Trademarks*